US011339418B2

(12) United States Patent
Stern et al.

(10) Patent No.: US 11,339,418 B2
(45) Date of Patent: May 24, 2022

(54) ANTIMICROBIAL SUSCEPTIBILITY TESTING AND MICROBIAL IDENTIFICATION

(71) Applicant: SELUX DIAGNOSTICS, INC., Charlestown, MA (US)

(72) Inventors: Eric Stern, Charlestown, MA (US); Kelly Flentie, Charlestown, MA (US); Kristin Baker, Charlestown, MA (US)

(73) Assignee: SELUX DIAGNOSTICS, INC., Charlestown, MA (US)

(*) Notice: Subject to any disclaimer, the term of this patent is extended or adjusted under 35 U.S.C. 154(b) by 121 days.

(21) Appl. No.: 16/516,184

(22) Filed: Jul. 18, 2019

(65) Prior Publication Data

US 2020/0024633 A1 Jan. 23, 2020

Related U.S. Application Data

(60) Provisional application No. 62/844,260, filed on May 7, 2019, provisional application No. 62/719,230, filed on Aug. 17, 2018, provisional application No. 62/701,146, filed on Jul. 20, 2018, provisional application No. 62/700,084, filed on Jul. 18, 2018.

(51) Int. Cl.

| | |
|---|---|
| ***C12Q 1/04*** | (2006.01) |
| ***C12Q 1/02*** | (2006.01) |
| ***G16B 40/10*** | (2019.01) |
| ***C12Q 1/689*** | (2018.01) |

(52) U.S. Cl.

CPC ............. *C12Q 1/045* (2013.01); *C12Q 1/025* (2013.01); *C12Q 1/689* (2013.01); *G16B 40/10* (2019.02)

(58) Field of Classification Search

None

See application file for complete search history.

(56) References Cited

U.S. PATENT DOCUMENTS

| | | | |
|---|---|---|---|
| 9,631,221 B1 | 4/2017 | Feng et al. | |
| 2006/0046246 A1 | 3/2006 | Zeng et al. | |
| 2015/0118688 A1 | 4/2015 | Weidemaier et al. | |
| 2017/0205426 A1* | 7/2017 | Stephenson, Jr .. | G01N 33/6848 |
| 2017/0211121 A1* | 7/2017 | Stern ........................ | C12Q 1/18 |
| 2017/0283846 A1* | 10/2017 | Moriyama ............... | C12Q 1/04 |

OTHER PUBLICATIONS

Tay et al., 2016 (Polymicrobial-Host Interactions during Infection; J Mol Biol (2016) 428, 3355-3371) (Year: 2016).*

Invitation to pay additional fees and, where applicable, protest fee( PCT Article 17(3)(a) and Rules 40.1 and 40.2(e)), for International application No. PCT/US2019/042485, dated Sep. 23, 2019, 3 pages.

Internatioanl Search Report and Written Opinion for International Application No. PCT/US2019/042485, dated Nov. 22, 2019, 18 pages.

Supplementary European Search Report for European Patent Application No. 19838030.5, dated Mar. 9, 2022.

Kohlmann, R., et al., "MALDI-TOF mass spectrometry following short incubation on a solid medium is a valuable tool for rapid pathogen identification from positive blood cultures", International Journal of Medical Microbiology, 305(4-5):469-479, Jun. 1, 2015 (Jun. 1, 2015).

Anderson, N. W., et al., "Effects of Solid-Medium Type on Routine Identification of Bacterial Isolates by Use of Matrix-Assisted Laser Desorption Ionization-Time of Flight Mass Spectrometry", Journal of Clinical Microbiology, 50(3):1008-1013, Mar. 1, 2012.

Altun, O., et al., "Rapid identification of bacteria from positive blood culture bottles by MALDI-TOF MS following short-term incubation on solid media", Journal of Medical Microbiology, 64(11): 1346-1352, Nov. 1, 2015.

* cited by examiner

*Primary Examiner* — Mary Maille Lyons

(57) ABSTRACT

Systems and methods for microbe identification (ID) in the context of phenotypic antimicrobial susceptibility testing (AST). Approaches for rapidly identifying polymicrobial samples are introduced that following perform one or more ID methods, such as matrix-assisted laser desorption/ionization time-of-flight mass spectrometry (MALDI-TOF), PCR, or DNA hybridization, following sample incubation in two or more different media, including at least one selective media. Parallel ID and AST workflows are provided that may reduce the time from sample to AST result.

20 Claims, 7 Drawing Sheets

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | POS | NEG | BG | BH | MCK | BE | BCC | BCA | BBE | KI | TS | IND | DNA | MO | PR | EMB | URE | MS | MSO | SS | CET | VP | CRT | MRG |
| B | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| C | POS | NEG | BG | BH | MCK | BE | BCC | BCA | BBE | KI | TS | IND | DNA | MO | PR | EMB | URE | MS | MSO | SS | CET | VP | CRT | MRG |
| D | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| E | POS | NEG | BG | BH | MCK | BE | BCC | BCA | BBE | KI | TS | IND | DNA | MO | PR | EMB | URE | MS | MSO | SS | CET | VP | CRT | MRG |
| F | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| G | POS | NEG | BG | BH | MCK | BE | BCC | BCA | BBE | KI | TS | IND | DNA | MO | PR | EMB | URE | MS | MSO | SS | CET | VP | CRT | MRG |
| H | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| I | POS | NEG | BG | BH | MCK | BE | BCC | BCA | BBE | KI | TS | IND | DNA | MO | PR | EMB | URE | MS | MSO | SS | CET | VP | CRT | MRG |
| J | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| K | POS | NEG | BG | BH | MCK | BE | BCC | BCA | BBE | KI | TS | IND | DNA | MO | PR | EMB | URE | MS | MSO | SS | CET | VP | CRT | MRG |
| L | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| M | POS | NEG | BG | BH | MCK | BE | BCC | BCA | BBE | KI | TS | IND | DNA | MO | PR | EMB | URE | MS | MSO | SS | CET | VP | CRT | MRG |
| N | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |
| O | POS | NEG | BG | BH | MCK | BE | BCC | BCA | BBE | KI | TS | IND | DNA | MO | PR | EMB | URE | MS | MSO | SS | CET | VP | CRT | MRG |
| P | MRC | MRL | MRMTL | MRMNS | MAR | MASU | MRT | MRX | MRD | MRAD | MRI | MRSOR | MRARB | MRE | MRAMG | MRMEL | MRGLY | MRMUC | PHD | DCL | DCO | DCA | KCN | COAG |

POS = NON-SELECTIVE; NEG = NO MEDIA; OTHERS DEFINED AS IN TABLES/TEXT

FIG. 2

| K. PNEUMONIAE (KP)-TO-E. COLI (EC) RATIO | MALDI FROM NONSELECTIVE BROTH |
|---|---|
| 0:1 (EC CONTROL) | EC (2.24) |
| 1:1 | KP (2.22) |
| 3:1 | KP (2.33) |
| 10:1 | KP (2.38) |
| 30:1 | KP (2.41) |
| 100:1 | KP (2.14) |
| 1:0 (KP CONTROL) | KP (2.29) |

FIG. 5B

| S. PNEUMONIAE-TO-S. LUGDUNENSIS RATIO | MALDI FROM NONSELECTIVE BROTH | MALDI FROM MANNITOL SALT BROTH |
|---|---|---|
| 0:1 (SL CONTROL) | SL (2.2) | SL (1.75) |
| 1:1 | SP (2.39) | SL (1.86) |
| 3:1 | SP (2.41) | SL (1.95) |
| 10:1 | SP (2.35) | SL (1.95) |
| 30:1 | SP (2.1) | NO ID ("NO PEAKS") |
| 100:1 | SP (2.36) | SL (1.73) |
| 1:0 (SP CONTROL) | SP (2.18) | NO ID ("NO PEAKS") |

FIG. 6

| E. COLI (EC)-TO-S. AUREUS (SA) RATIO | MALDI FROM NONSELECTIVE BROTH | MALDI FROM MANNITOL SALT BROTH | MALDI FROM MACCONKEY BROTH |
|---|---|---|---|
| 0:1 (SA CONTROL) | SA (2.53) | | |
| 1:1 | EC (2.1) | SA (2.48) | EC (2.15) |
| 3:1 | SA (2.08) | SA (2.46) | EC (2.26) |
| 10:1 | SA (2.22) | SA (2.43) | EC (2.3) |
| 30:1 | SA (2.49) | SA (2.45) | EC (2.29) |
| 100:1 | EC (2.19) | SA (2.56) | EC (2.19) |
| 1:0 (EC CONTROL) | EC (2.17) | | |

FIG. 7

ANTIMICROBIAL SUSCEPTIBILITY TESTING AND MICROBIAL IDENTIFICATION

CROSS REFERENCE TO RELATED APPLICATIONS

This application claims the benefit of priority to U.S. Provisional Patent Application No. 62/700,084, filed Jul. 18, 2018, and U.S. Provisional Patent Application No. 62/701,146, filed on Jul. 20, 2018, and U.S. Provisional Patent Application No. 62/719,230, filed on Aug. 17, 2018, and 62/844,260, filed on May 7, 2019. The disclosure of each of the preceding applications is hereby

FIELD

The present disclosure relates to methods for antimicrobial susceptibility testing and microbial identification.

BACKGROUND

Antimicrobial-resistant microbial infections are associated with poor clinical outcomes including increased morbidity, mortality, and healthcare costs among infected patients. The prevalence of these organisms in the United States has steadily increased over the last 30 years. Phenotypic antimicrobial susceptibility testing (AST) of microorganisms is critical for informing physicians of appropriate therapeutic regimens. Using current methods, AST determination typically requires a minimum of eight hours, rendering it an overnight process due to shift work in many clinical microbiology laboratories. While awaiting a determination from current AST methods, patients are often administered broad-spectrum antimicrobials which often have significant detrimental effects on patient health and/or contribute to the growing antimicrobial resistance epidemic. Furthermore, this time delay obtaining accurate antimicrobial treatment information increases patient stays in hospitals, thereby increasing costs and inconvenience to the patient.

Against this backdrop, government and industry stakeholders have proposed rules to promote antimicrobial stewardship in hospitals. However, antimicrobial stewardship efforts may be complicated by the limitations of current AST methods and antimicrobial prescribing practices. The inventors have previously disclosed a method for rapid AST, that may reduce the time required for AST determinations and facilitate antimicrobial stewardship. For example, AST systems and methods utilizing fluorescent probes that bind microorganism surfaces are described in commonly owned U.S. Pat. No. 9,834,808. These systems and methods are advantageous in that they address this need in a cost-effective manner and can be compatible with existing assay hardware components.

AST results may be complicated in cases where a sample comprises more than one species of microbe, as results are likely to be dominated by antimicrobial effects on the most rapidly growing species in the sample, which may or may not be the species responsible for infection. This is addressed in current AST practice using a "purity plate," typically a solid phase culture to isolate and identify individual bacterial colonies. Because culturing and analyzing colonies typically takes at least 18 hours and some clinical laboratories do not report AST results until purity plate results are available, the use of purity plates may introduce delays into AST workflows and, consequently, the delivery of targeted therapy to patients.

SUMMARY

The present disclosure provides improved rapid AST systems and methods in which isolation and identification of microbial species and strains is accelerated, potentially reducing the time required for delivery of AST results from patient samples. In one aspect, the disclosure relates to a method for assessing a number of different microbial species in a sample, e.g., assessing whether a sample is mono- or poly-microbial. The method utilizes a selective/differential growth panel (SDGP) comprising a plurality of selective and/or differential growth media, which is inoculated and incubated under conditions suitable for microbial growth. This method may include inoculating a selective/differential growth panel (SDGP) with a sample, the SDGP comprising first and second growth media, wherein (a) the first and second growth media are differential or selective growth media, (b) each selective growth medium comprises (i) one or more compounds suitable for promoting growth of a subset of microorganisms, and/or (ii) one or more compounds that inhibit growth of a subset of microorganisms, (c) each differential growth medium comprises a substrate for an enzyme expressed by a group of microorganisms, and (d) wherein a reaction of the substrate catalyzed by the enzyme produces a reaction product. The SDGP may be incubated under conditions suitable for microbial growth. First and second subsamples may be selected from each of the first and second selective growth media of the SDGP. For each subsample or colony, at least one assay may be performed to detect one or more of a microorganism present in the selective growth media, the substrate, and the reaction product. For each subsample, based on the detection of the microorganism, substrate, and/or the reaction product, microbial species present in the subsample may be identified. The groups of microbial species present in each of the subsamples may be compared to determine if the sample is monomicrobial or polymicrobial, and optionally, it may be reported to a user that the sample is monomicrobial or polymicrobial.

In some embodiments, the method may further comprise reporting to a user the microbial species present in at least one subsample. At least one of the selective or differential growth media may comprise an immunoglobulin-G (IgG) or fragment thereof. The IgG or fragment thereof may comprise one or more optical labels. The method may further comprise performing a coagulase assay and based on the results of the coagulase assay and the results from the selective and/or differential media, determining whether the sample is monomicrobial or polymicrobial. The SDGP may comprise a minimum of 4, 6, 8, 10, 12, 14, 16, 18, 20 reservoirs. One or more reservoirs on the SDGP may comprise non-selective media. A first SDGP may be used if a Gram stain performed on the sample is positive and a second SDGP may be used if the Gram stain is negative. At least one SDGP reservoir may comprise at least one probe compound. Probe compounds may include, but are not limited to, surface-binding agents, locked nucleic acids, peptide nucleic acids, other fluorescence in situ hybridization probes. Probes may comprise one or more optical labels. The assay to identify a microbe may comprise generating a mass spectrum for the first and second subsamples and comparing the mass spectrum to one or more libraries of standard mass spectra for microbes. The step of generating a mass spectrum may utilize one or more of the following: a time-offlight (TOF) detector, a static electric and/or magnetic sector as a mass analyzer, a quadrupole mass analyzer, and an ion trap. The step of generating a mass spectrum may utilize one or more of the following ionization sources: chemical ionization, plasma and glow discharge, electron impact, electrospray ionization, desorption electrospray ionization, fast-atom bombardment, field ionization, laser ionization, liquid-extraction surface analysis, matrix-assisted laser desorption ionization. The step of generating a mass spectrum may comprise spotting a subsample from a well reservoir of the SDGP onto a plate for matrix-assisted laser desorption ionization TOF mass spectrometry (MALDI-TOF), and performing MALDI-TOF, thereby generating the mass spectrum. The spotting and MALDI-TOF may be performed by an automated or semi-automated instrument. The analysis of the mass spectrum may reflect proteins and/or glycolipids of the microbe. The mass spectrum analysis may comprise imaging. One or more probe compounds comprised in one or more SDGP reservoirs may be identified by mass spectrometry. The microorganisms may be concentrated before spotting on the MALDI-TOF target. The microorganisms may be concentrated by centrifugation before spotting on the MALDI-TOF target. The microorganisms may be concentrated to a pellet before spotting on the MALDI-TOF target. One or more wash steps may be performed prior to spotting on the MALDI-TOF target. One or more optical measurements of SDGP reservoirs comprising absorbance, fluorescence, luminescence, time-gated luminescence may be performed. One or more optical measurement may be performed prior to and/or following washing. One or more biochemical assays may be performed in the first or second selective/differential growth media before MALDI-TOF is performed. MALDI-TOF may be used determine the presence of one or more resistance markers. Resistance markers may be determined from microorganisms derived from a non-selective media and/or antimicrobial-comprising media. The step of generating a mass spectrum may comprise utilizing a gas and/or liquid chromatograph for sample separation prior to mass spectroscopy. The microbial species may be bacteria, fungi, protozoa, and/or archaea. The microbial species may further comprise one or more of the following: *Escherichia* spp., *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Citrobacter* spp., *Morganella* spp., *Aerococcus* spp., *Aeromonas* spp., *Achromobacter* spp., *Actinomyces* spp., *Bacillus* spp., *Bartonella* spp., *Bordetella* spp., *Brucella* spp., *Burkholderia* spp., *Campylobacter* spp., *Chlamydia* spp., *Chlamydophila* spp., *Clostridium* spp., *Corynebacterium* spp., *Ehrlichia* spp., *Francisella* spp., *Gardenerella* spp., *Haemophilius* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Providencia* spp., *Rickettsia* spp., *Raoultella* spp., *Salmonella* spp., *Serratia* spp., *Shigella* spp., *Stenotrophomonas* spp., *Treponema* spp., *Ureaplasma* spp., *Vibrio* spp., *Yersinia* spp., and combinations thereof. The microbial species may comprise a member of the Enterobacteriaceae family. The fungi may be selected from the group consisting of *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix, Exserohilum, Cladosporium*, ringworm, mucormycetes, and combinations thereof.

In some embodiments, the patient sample may be one or more of the following: blood, urine, cerebrospinal fluid, synovial fluid, an aspirate, a lavage, a wound swab, or a respiratory sample. The patient sample may further be cultured prior to inoculating the SDGP. Exemplary culture methods include, but are not limited to, blood culture, other liquid culture, solid culture, and particularly solid culture plates on which colonies are collected before complete growth, which may be termed "smudge plates."

In some embodiments, the SDGP comprises two or more independent reservoirs on a single consumable. Further, the SDGP reservoirs may be inoculated with a robotic liquid handler. Also, the robotic liquid handler may inoculate both SDGP reservoirs and one or more reservoirs of antimicrobial susceptibility test (AST) panels. Further, the SDGP and AST reservoirs may be on the same consumable. In yet another embodiment, two or more SDGP reservoirs may be present on a consumable such that two or more patient samples may be inoculated into that consumable.

In some embodiments, the assay may comprise identifying a nucleic acid sequence of the microorganism following SDGP incubation. The assay may comprise sequencing the nucleic acid, hybridizing a probe to the nucleic acid, or performing an enzyme catalyzed reaction on the nucleic acid. The microbial incubation in SDGP media may be performed for between 1 and 10 hours, 2 and 8 hours, 3 and 7 hours, 4 and 6 hours. Each selective medium may comprise of one or more media selected from the group consisting of: *Streptococcus* enrichment broth, Fraser broth, Giolitti Cantoni broth, *Streptococcus faecalis* media, sodium lauryl sulfate, tellurite, and those listed in Table 1. Each differential reservoir of the SDGP may comprise one or more of media is comprised of indole, methyl red, Voges-Proskauer (VP), citrate utilization (CRT), and selective sugar fermentation tests [e.g., glucose (MRG), cellobiose (MRC), lactose (MRL), mannitol (MRMTL), mannose (MRMNS), raffinose (MRR), sucrose (MRSU), trehalose (MRT), xylose (MRX), dulcitol (MRD), adonitol (MRAD), inositol (MRI), sorbitol (MRSOR), arabinose (MRARB), maltose, alpha-methyl-D-glucoside (MRAMG), erythritol (MRE), melibiose (MRMEL), arabitol, glycerol (MRGLY), and/or mucate (MRMUC) fermentation], citrate reduction test (CRT); phenylalanine deaminase test (PHD); triple sugar iron with or without hydrogen sulfide detection; urease test; decarboxylation tests using lysine (DCL), ornithine (DCO), arginine (DCA); utilization of malonate, acetate, and/or tartrate; gelatin hydrolysis test; esculin hydrolysis test; lipase test; DNase test; growth in potassium cyanide (KCN); growth tests with novobiotin; coagulase tests (COAG); Decarboxylation of amino acids; Glucuronidase activity (GUS); beta-galactosidase activity; intrinsic fluorescence; Esculin hydrolysis; Tryptophan hydrolysis etc. The SDGP may comprise liquid media. The SDGP may comprise solid media. The SDGP may comprise liquid and solid media. Identification may be reported to the species, genus, family level. Gram type may be reported. One or more resistance markers may be reported. Resistance to one or more antimicrobials may be reported.

In some embodiments, at least one of the selective and/or differential growth media comprises an immunoglobulin-G (IgG) or fragment thereof, and the step of performing at least one assay to identify a reaction product in the colony or subsample comprises detecting the presence or absence at least one signal characteristic of the IgG or fragment thereof.

In some embodiments, where one or more coagulase assays are performed and the results of these one or more assays are utilized together with the results from the selective and/or differential media to determine if the sample is monomicrobial or polymicrobial.

Assays used in various embodiments include mass spectroscopy, e.g., matrix-assisted laser desorption/ionization time-of-flight mass spectrometry (MALDI-TOF) and/or amplifying a nucleic acid sequence, hybridizing a probe to a nucleic acid, or sequencing a nucleic acid from the colony or sample. When mass spectrometry assays are used, the method optionally includes one or more of (a) spotting a microbial pellet or fluid from a well of the SDGP onto a MALDI-TOF plate and performing MALDI-TOF, (b) performing MALDI-TOF using an automated/semi-automated instrument, and/or performing one or more biochemical assays in the selective media prior to performing MALDI-TOF. The method optionally includes concentrating the microorganisms before spotting on the MALDI-TOF target. The method further optionally includes concentrating the microorganisms to a pellet before spotting on the MALDI-TOF target.

Assays used in various embodiments further may include generating a mass spectrum for the first and second subsamples and comparing the mass spectrum to one or more libraries of standard mass spectra for microbes. Other embodiments may further comprise generating a mass spectrum utilizing a gas and/or liquid chromatograph for sample separation prior to mass spectroscopy.

In other embodiments, one or more biochemical assays may be performed in the first or second SDGP before MALDI-TOF is performed.

Continuing with this aspect of the disclosure, in some embodiments the SDGP is a multi-well plate (e.g., a 48, 96 or 384 well plate) and a plurality of wells of the plate comprise different selective media, such as those listed in Table 1 herein. The method also optionally includes performing antimicrobial susceptibility testing (AST) on the sample and releasing the result of identification and AST if the sample is not flagged as polymicrobial (i.e., determined to be monomicrobial). In some embodiments, the SDGP is a plate comprising a plurality of selective media in solid form, in which case the step of selecting a subsample or colony may comprise taking an image of the SDGP, identifying a microbial colony in the image, and contacting the microbial colony with an implement, thereby lifting at least a portion of the colony off of the solid medium (e.g., for spotting onto a MALDI-TOF plate). The implement be a swab in some embodiments. In the various embodiments according to this aspect of the invention, a growth control well is optionally utilized, which comprises a non-selective medium inoculated with the sample. Growth is assessed in the growth control well after incubation and compared to a predetermined threshold: if the level of growth meets or exceeds the threshold, a colony or subsample is selected and the method proceeds; if the level of growth is below the threshold, the SDGP is incubated further, and the level of growth is optionally checked in the growth control well again until the threshold is met.

In another aspect, the disclosure relates to a selective/differential growth panel (SDGP) comprising a plurality of fluid reservoirs, each comprising one of a plurality of different selective growth media. The SDGP optionally includes at least one fluid reservoir comprising a non-selective culture medium, and/or an AST panel, including a second plurality of fluid reservoirs defining dilution series for a plurality of antimicrobials.

In another aspect, the disclosure relates to a method for performing microbial identification (ID) testing sequences, which includes inoculating a SDGP with a sample as described for other aspects of the disclosure, then loading the SDGP into an automated system for performing ID testing sequences and operating the system to incubate and agitate the SDGP, spot a portion of a fluid culture or microbial pellet from each of the plurality of wells of the SDGP onto a MALDI-TOF plate, add a matrix solution and solvent, and perform MALDI-TOF to generate a mass spectrum for each of the plurality of wells. In some cases, the SDGP is centrifuged before MALDI target spotting to form a microbial pellet in each of the plurality of wells. As described above in other aspects of the disclosure, the SDGP may include an AST panel defining a plurality of dilution series for a plurality of antimicrobials and at least one growth control well lacking an antimicrobial and comprising a non-selective growth medium. In these cases, the method also optionally includes the following steps: after incubating and agitating the SDGP for a predetermined period, assessing a level of microbial growth in the at least one growth control well; and if the microbial growth exceeds a predetermined threshold, performing at least one endpoint assay on each of the plurality of dilution series and identifying a minimum inhibitory concentration for at least one of the plurality of antimicrobials.

In yet another aspect, the disclosure relates to a system for assessing whether a patient is polymicrobial, wherein the system determines and reports a species identification.

In an embodiment according to this aspect of the disclosure, at least one of the selective and/or differential growth media comprises an IgG or fragment thereof, and the detection module is configured to detect at least one signal characteristic of the IgG or fragment thereof.

In another embodiment, one or more coagulase assays are performed and the results of these one or more assays are utilized together with the results from the selective and/or differential media to determine if the sample is monomicrobial or polymicrobial.

In another embodiment, the information about the substrate and/or the reaction product comprises a mass spectrum, and the processor is configured to compare the mass spectrum to one or more libraries of standard mass spectra for microbes.

In yet another embodiment, the step of generating a mass spectrum may utilize a time-of-flight (TOF) detector, a static electric and/or magnetic sector as a mass analyzer, a quadrupole mass analyzer, or an ion trap. This system further comprises the mass spectrum being generated by matrix-assisted laser desorption/ionization time-of-flight mass spectrometry (MALDI-TOF), and the performance of MALDI-TOF. This system further comprises an automated instrument that (a) deposits material from each of the differential growth media onto a plate which is used for MALDI-TOF and (b) performs MALDI-TOF. Further embodiments of the system include those wherein one or more biochemical assays are performed in the first or second differential growth media before MALDI-TOF is performed.

In another embodiment, the step of generating a mass spectrum may utilize one or more of the following ionization sources: chemical ionization, plasma and glow discharge, electron impact, electrospray ionization, fast-atom bombardment, field ionization, laser ionization, or matrix-assisted laser desorption ionization.

In another aspect, this disclosure describes a system for assessing whether a patient sample is polymicrobial. This system may comprise a selective/differential growth panel (SDGP), comprising first and second selective and/or differential growth media for inoculation with a sample derived from a patient, wherein (a) each selective growth medium comprises one or more compounds suitable for promoting growth of a subset of microorganisms, (b) each selective growth medium comprises one or more compounds that inhibit growth of a subset of microorganisms, (c) each differential growth medium comprises a substrate for an enzyme expressed by a group of microorganisms, and (d) wherein a reaction of the substrate catalyzed by the enzyme produces a reaction product and a processor that is configured to (1) receive information about the microorganism, substrate and/or the reaction product from each selective/differential growth medium from the detection module and, based on that information, determine the presence of one or more microbial species in each media, and (2) compare the microbial species assigned to each of the selective and/or differential growth media and, (3) if only a single species is identified, reporting its identification, or if two or more groups species are identified, flagging the sample as polymicrobial and optionally reporting the identifications.

In some embodiments, the system determines and reports species identification. At least one or the selective and/or differential growth media may comprise a labeled or bound IgG or fragment thereof, and the detection module is configured to detect at least one signal characteristic of the labeled or bound IgG or fragment thereof. One or more coagulase assays may be performed and the results of these one or more assays may be utilized together with the results from the selective and/or differential media to determine if the sample is monomicrobial or polymicrobial. The information about the substrate and/or the reaction product may comprise a mass spectrum, and the processor may be configured to compare the mass spectrum to one or more libraries of standard mass spectra for microbes. The step of generating a mass spectrum may utilize one or more of the following: a time-of-flight (TOF) detector, a static electric and/or magnetic sector as a mass analyzer, a quadrupole mass analyzer, and an ion trap. The step of generating a mass spectrum may utilize one or more of the following ionization sources: chemical ionization, plasma and glow discharge, electron impact, electrospray ionization, fast-atom bombardment, field ionization, laser ionization, matrix-assisted laser desorption ionization. The mass spectrum may be generated by matrix-assisted laser desorption/ionization time-of-flight mass spectrometry (MALDI-TOF), and the performance of MALDI-TOF. The system may further comprise an automated instrument that (a) deposits material from each of the differential growth media onto a plate which is used for MALDI-TOF and (b) performs MALDI-TOF. One or more biochemical assays may be performed in the first or second differential growth media before MALDI-TOF is performed. The patient sample may be one or more of the following: blood, urine, cerebrospinal fluid, synovial fluid, an aspirate, a lavage, a wound swab, or a respiratory sample. The patient sample may be cultured prior to a selective/differential growth panel (SDGP) preparation. The SDGP may comprise two or more reservoirs on a single consumable. The SDGP reservoirs may be inoculated with a robotic liquid handler. The robotic liquid handler may inoculate both an SDGP reservoir and one or more reservoirs of an antimicrobial susceptibility test (AST) panel. The two or more reservoirs may comprise an SDGP and an AST reservoir. Two or more of the same SDGP reservoirs may be present on a consumable such that two or more patient samples may be inoculated into the consumable. At least one of the selective or differential growth media may comprise an immunoglobulin-G (IgG) or fragment thereof. The IgG or fragment thereof may comprise one or more optical labels. The system may be configured to perform a coagulase assay and based on the results of the coagulase assay and the results from the selective and/or differential media, the system may be configured to determine whether the sample is monomicrobial or polymicrobial. The SDGP may comprise a minimum of 4, 6, 8, 10, 12, 14, 16, 18, 20 reservoirs. One or more reservoirs on the SDGP may comprise non-selective media. A first SDGP may be configured for Gram positive microbes and a second SDGP may be configured for Gram negative microbes. At least one SDGP reservoir may comprise at least one probe compound. Probe compounds may include, but are not limited to, surface-binding agents, locked nucleic acids, peptide nucleic acids, other fluorescence in situ hybridization probes. Probes may comprise one or more optical labels. The assay may be configured to identify a microbe comprising generating a mass spectrum for the first and second subsamples and comparing the mass spectrum to one or more libraries of standard mass spectra for microbes. The system may comprise a mass spectrometer selected from the group consisting of: a time-of-flight (TOF) detector, a static electric and/or magnetic sector as a mass analyzer, a quadrupole mass analyzer, and an ion trap. The system may comprise an ionization source selected from the group consisting of: chemical ionization, plasma and glow discharge, electron impact, electrospray ionization, desorption electrospray ionization, fast-atom bombardment, field ionization, laser ionization, liquid-extraction surface analysis, matrix-assisted laser desorption ionization. The system may be configured to spot a subsample from a reservoir of the SDGP onto a plate for matrix-assisted laser desorption ionization TOF mass spectrometry (MALDI-TOF), and perform MALDI-TOF, thereby generating the mass spectrum, with an automated or semi-automated instrument. The system may be configured to concentrate the microorganisms before spotting on the MALDI-TOF target. The system may be configured to concentrate the microorganisms to a pellet by centrifugation before spotting on the MALDI-TOF target. The system may be configured to perform one or more wash steps prior to spotting on the MALDI-TOF target. The system may be configured to perform one or more optical measurements of SDGP reservoirs comprising absorbance, fluorescence, luminescence, time-gated luminescence. The system may be configured to generate a mass spectrum comprising utilizing a gas and/or liquid chromatograph for sample separation prior to mass spectroscopy. The SDGP may comprise two or more independent reservoirs on a single consumable. The SDGP reservoirs may be inoculated with a robotic liquid handler. The robotic liquid handler may inoculate both SDGP reservoirs and one or more reservoirs of antimicrobial susceptibility test (AST) panels. The SDGP and AST reservoirs may be comprised on the same consumable. Two or more of the same SDGP reservoirs may be present on a consumable such that two or more patient samples may be inoculated into that consumable. The assay may be configured to identify a nucleic acid sequence of the microorganism following SDGP incubation. The assay may be configured to comprise sequencing the nucleic acid, hybridizing a probe to the nucleic acid, or performing an enzyme catalyzed reaction on the nucleic acid.

The foregoing listing is intended to be exemplary rather than limiting, and skilled artisans will appreciate additional aspects of the disclosure, as well as modifications to the aspects and embodiments described above.

BRIEF DESCRIPTION OF THE DRAWINGS

FIG. 2 shows exemplary liquid-phase purity plate designs according to certain embodiments of this disclosure.

FIG. 5B shows MALDI result for five different mixed ratios of *K. pneumoniae* and *E. coli.*

FIG. 6 shows MALDI results for five different spiked ratios of *S. pneumoniae* to *S. lugdunensis* and Bruker BioTyper MALDI-TOF results after 4-hour growth in non-selective media (Mueller-Hinton broth, MHB) and Mannitol salt broth. While not wishing to be bound by any theory, it is believed that the comparatively slow growth rate of *S. lugdunensis* in MHB enables *S. pneunomiae* to dominate MALDI signals in samples from non-selective media. By contrast, MALDI analysis of samples grown in selective Mannitol salt broth media reveal the presence of *S. lugdunensis* in the samples.

FIG. 7 presents MALDI results for five different spiked ratios of *E. coli* to *S. aureus* and Bruker BioTyper MALDI-TOF results after 4-hour growth in nonselective media (Mueller-Hinton broth), or selective media: Mannitol salt broth, and MacConkey broth. MALDI identification of samples growth in both selective media reveal the presence of two bacterial species in the samples.

DESCRIPTION

Overview

Figure 1:
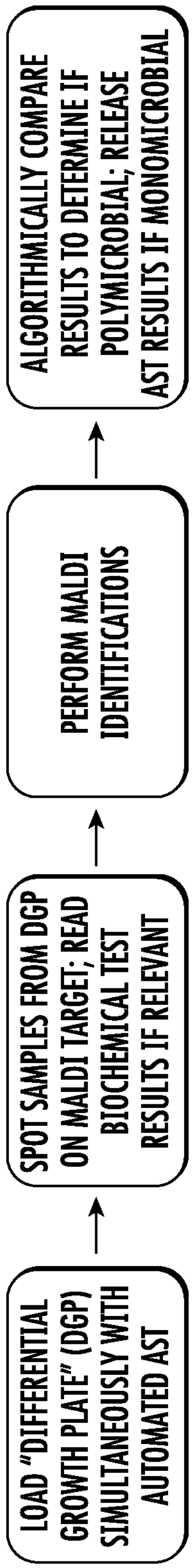
FIG. 1 shows an AST workflow according to certain embodiments of the disclosure.

The systems and methods of the present disclosure are, generally, addressed to reducing the time required for performance and delivery of antibiotic susceptibility testing ("AST") results by reducing assay time associated with microbial identification ("ID"). Many clinical laboratories perform ID analyses using matrix-assisted laser desorption/ionization time-of-flight mass spectrometry (MALDI-TOF) platforms. Because mass spectra are complex, ID is typically achieved by comparing a spectrum from a clinical sample to a database of microbial standards. It will be apparent to the skilled artisan that the complexity of these spectra will be increased by the presence of more than one microbe in a sample, and that a contaminating or co-culturing species may complicate or prevent ID calls. In current industry standard workflows, a purity plate is run overnight on non-selective agar in parallel with AST processing from the same bacterial inoculum used for AST. This workflow ensures AST results derive from a single bacterial species and/or strain. Although some clinical microbiology laboratories release AST results to the clinic before purity plates are available, many require monomicrobial sample confirmation by the purity plate before AST results are released to the clinic. While waiting for purity plate results before AST result release helps ensure AST results will be actionable, it may introduce delay into the reporting of AST data, and consequently delay the transition of patients to targeted therapies.

Multiple strategies are employed in the various embodiments of this disclosure to reduce the time required for AST results to be relayed for a given patient sample and for prescribing decisions based on those results to be made. First, in certain embodiments of this disclosure samples for microbial ID and/or monomicrobial confirmation ("purity") are cultured using conditions selective for the growth of particular microbes or categories of microbes followed by subjecting these cultured samples to ID by a suitable method.

Table 1, below, lists representative selective media that may be used in systems and methods of this disclosure. Selective media suppresses, inhibits, reduces, etc., the growth of microorganisms other than the specific microorganism types (i.e., species, family, genus, etc.) it is designed to support, but those of skill in the art will appreciate that the degree of suppression, inhibition, reduction, etc., may depend on the microbes. These media may be used in solid or liquid form. Other selective media may include *Streptococcus* enrichment broth, Fraser broth, Giolitti Cantoni broth, *Streptococcus faecalis* media, sodium lauryl sulfate, and tellurite.

TABLE 1

Selective growth media:

| MEDIA | MICROORGANISM GROWTH |
|---|---|
| Brilliant green media (BG) | *Salmonella* selective |
| Brain heart infusion media with vancomycin (BHI) | Vancomycin-resistant Enterococci selective |
| MacConkey media and purple media (MCK) | Gram negatives selective |
| Bile esculin media (BE) | Streptococci and enterococci selective |
| BCYE selective media with CCVC or CAV (BCC, BCA) | *Legionella* selective |
| BBE/LKV | *Bacteroides fragilis* and obligate anaerobes selective |
| Klinger iron media (KI), triple sugar media (TS) | Differentiate Enterobacteriaceae |
| Indole media (IND) | Differentiate Enterobacteriaceae |
| DNAse test media (DNA) | Differentiate Enterobacteriaceae and Staphylococci |
| Mio medium (MIO) | Differentiate Enterobacteriaceae (after addition of Kovacs reagent) |
| Phenol red media (PR) | Differentiate Enterobacteriaceae |
| Eosin-Methylene blue (EMB) media | Differentiate Enterobacteriaceae |
| Urea media (URE) | Differentiate Enterobacteriaceae |
| Mannitol salt media (with and without oxacillin) (MS, MSO) | Staphylococci selective (differential for MRSA) |
| Selective strep media (SS) | Streptococci selective |
| Cetrimide media (CET) | Pseudomoni selective |
| Leeds *Acinetobacter* media (LAB) | *Acinetobacter* selective |

TABLE 2

Exemplary Gram-positive and Gram-negative microbes

| Gram-Negative | Gram-Positive |
|---|---|
| *Serratia* | *Stapylococcus* - *S. epidermidus* |
| | *S. lugdunensis* |
| | *S. aureus* |
| Proteae - *Proteus mirabilis* | *Lactobacillus* |
| *Stenophomnas maltophila* | *Bacillus* |
| *Enterobacter* | *Enterococcus* - *E. Faecalis* |
| | *E. faecium* |
| *Achromobacter* | *Listeria monocytogenes* |
| *Citrobacter* - *Citrobacter* AmpC | *Corynebacterium ieikeium* |
| *Salmonella* | *Micrococcus* |
| *E. coli* | *Streptococcus* - *S. agalactiae* |
| | *S. pyogenes* |
| | *S. pneumoniae* |
| | Strep viridans - Strep Bovis group |
| *Klebsiella* | |
| *Pseudomonas* - *P. Aeruginosa* | |
| *Acinetobacter* | |
| *Haemophilus influenzae* | |
| *Neisseria meningitidis* | |

An exemplary workflow utilizing selective or differential media according to this disclosure is depicted in FIG. 1. A “differential growth plate” and/or “differential growth panel” comprising one or more differential or selective media is inoculated with a sample and incubated under conditions that support microbial growth. For selective media, these conditions may include different (e.g., elevated) temperatures and controlled $CO_2$ levels. One or more non-selective media may also be included on the plate and/or panel. Following incubation, the sample is harvested and prepared for microbial ID using any suitable method, including without limitation detection of specific nucleotide sequences, e.g., by sequencing (Sanger or Next-Gen), polymerase chain reaction (PCR), hybridization with a probe, sequence specific binding by CRISPR-Cas9 or CRISPR-Cpf1 etc., detection of specific antigens or epitopes using antibodies, aptamers, etc., and/or by mass spectrometry, e.g., using MALDI-TOF as described below.

One advantage of growing ID samples in selective media growth is that that the breadth of relevant species to be detected in each condition is limited. For example, if a media only supports the growth of Staphylococci, only primers for Staphylococci are necessary for genetic ID and only Staphylococci datasets need be interrogated for MALDI-TOF ID.

Microbial samples may be added directly to the differential growth plate or panel, or may be processed (e.g., concentrated) prior to addition. In some embodiments, the differential growth plate includes a substrate (e.g., an enzymatic substrate) that indicates a species or strain of microbe is present or absent in a growth condition. Alternatively or additionally, the differential growth plate may include an agent, such as an antibody or fragment thereof, an aptamer, an antisense oligonucleotide, etc. that recognizes an antigen or a nucleotide sequence that indicates a species or strain of microbe is present in a growth condition.

Differential growth panels according to this disclosure generally utilize a cassette or plate comprising a plurality of fluid reservoirs e.g., 48, 96, 384 etc. wells. Two or more selective media are provided to different wells of the cassette, and at least one well of the cassette may include a non-selective medium such as Mueller-Hinton broth, tryptic soy agar with lysed equine whole blood, for example as a growth control well. In some cases, a cassette may include two or more substantially arrays of wells comprising different selective or non-selective media, such that two or more samples (e.g., from two or more patients) may be run on a single cassette.

An exemplary 384-well differential growth panel layout is shown in FIG. 2. The panel comprises a plurality of identical 48-well arrays; in use, each array is inoculated with a different sample, enabling multiple (up to 8) samples to be processed in parallel. Within each array, in addition to selective media, there may be included one or more biochemical or binding test wells (e.g., wells that include an enzymatic substrate or binding agent that indicates the presence or absence of one or more species of microorganism) that may provide additional species information, such as for differentiating between Enterobacteriaceae and Staphylococci. Plates comprising broth and tests only for gram-positive or gram-negative bacteria may be utilized but it may be preferable to run all broths and tests on a single plate. By separating plates, for example, different growth conditions may be used for different microorganism types. Specific media and/or tests requiring different growth conditions may also be run in parallel on different plates. When liquid-phase plates are utilized as the primary means for polymicrobial identification, it may be advantageous to run solid-phase culture in parallel, as this method may provide isolates that can be utilized for ID and/or AST in the case of a polymicrobial sample.

The selective/differential growth panel comprises various media which either selectively grow or inhibit a subset of microorganisms. Each selective growth medium contains one or more compounds that, variously, promotes or facilitates the growth of, or inhibits or prevents the growth of, a microorganism species or group of species. Each differential growth medium contains one or more substrates for an enzyme-catalyzed reaction that is characteristic of a species or group of species of microorganisms. When the substrate in the differential growth medium reacts with the microorganism in the enzyme-catalyzed reaction, a reaction product is produced and/or the reaction substrate is eliminated. Based on the presence or absence, or the relative quantities, of the substrate and/or reaction product, a user can infer the presence or absence of a particular microbial species or group of species in an inoculum.

Differential growth media can be used to differentiate between *Staphylococcus aureus* and coagulase-negative Staphylococci (CONS). An example of a differential growth media is seen in the use of Immuoglobulin G (IgG) in the growth media. The protein A receptor of *Staphylococcus aureus* will bind to IgG, while other strains of *Staphylococcus* will not. Therefore, if *Staphylococcus aureus* is present in the sample and binds to IgG, there will be an absence of any signal which is characteristic of IgG or a fragment thereof. The presence of IgG may be detected e.g., optically with a fluorescent label. Unbound IgG may be removed through centrifugation. Another example is the use of coagulase assays. In these assays, the presence of coagulase as a reaction product indicates the presence of *Staphylococcus aureus* in the sample. After depletion of *S. aureus* in a coagulase assay, other individual growth tests may be performed to identify remaining Staphylococci strains.

While selective growth media promotes the selective growth of microbial species and/or strains, it may be desirable in some cases to differentiate between species or strains that grow similarly in a given selective growth medium (e.g., to differentiated among Enterobacteriaceae). A number of suitable reagents for differentiating between such species or strains are known in the art, including without limitation indole, methyl red, Voges-Proskauer (VP), citrate utilization (CRT), and selective sugar fermentation tests [e.g., glucose (MRG), cellobiose (MRC), lactose (MRL), mannitol (MRMTL), mannose (MRMNS), raffinose (MRR), sucrose (MRSU), trehalose (MRT), xylose (MRX), dulcitol (MRD), adonitol (MRAD), inositol (MRI), sorbitol (MRSOR), arabinose (MRARB), maltose, alpha-methyl-D-glucoside (MRAMG), erythritol (MRE), melibiose (MRMEL), arabitol, glycerol (MRGLY), and/or mucate (MRMUC) fermentation], citrate reduction test (CRT); phenylalanine deaminase test (PHD); triple sugar iron with or without hydrogen sulfide detection; urease test; decarboxylation tests using lysine (DCL), ornithine (DCO), arginine (DCA); utilization of malonate, acetate, and/or tartrate; gelatin hydrolysis test; esculin hydrolysis test; lipase test; DNase test; growth in potassium cyanide (KCN); growth tests with novobiotin; coagulase tests (COAG); Decarboxylation of amino acids; Glucuronidase activity (GUS); beta-galactosidase activity; intrinsic fluorescence; Esculin hydrolysis; etc. In some embodiments of the present disclosure, one or more of the foregoing reagents is added to a selective growth medium to render it a differential growth medium. Without limiting the foregoing, it may be advantageous in some cases to perform additional tests in parallel to assessments of growth in selective media. For example, in order to differentiate *Staphylococcus aureus* from coagulase-negative Staphylococci (CONS) it may be useful to perform coagulase and/or individual growth tests in Staphylococci-selective media, such as mannitol salt, with one or more tests to identify *S. aureus*, e.g., through the use of immunoglobulin G (IgG) that binds to Protein A, a surface protein which is expressed by *S. aureus* but not by coagulase-negative *Staphlococci*. Relative growths in non-depleted and depleted wells are then compared and analyzed.

A number of readouts may be used in differentiating between species or groups of species grown in differential growth media, including without limitation light absorption or transmission. For example, if eosin methylene blue (EMB) media is used, optical interrogation by absorbance is used to interpret colony colors. As is described in US pre-grant publication no. 2018/0088141, bacteria grown in liquid culture, e.g., on test panels, may be pelleted by centrifugation, followed by media aspiration (and potential subsequent washing), followed by contacting with a specific stain or other reagent. These methods permit evaluations of microbial colonies grown in the liquid-phase that have previously been limited to colonies grown in the solid phase.

In certain embodiments of this disclosure, mass spectrometry is used as a readout of one or more differential growth media. Mass spectrometry, and specifically MALDI-TOF, can be used to detect the products of enzymatic reactions which are representative of specific microbial species. Once a library of mass spectra has been established, mass spectrometry is an efficient and cost-effective manner of identifying microorganisms present in a sample. Due to the design of the MALDI-TOF plate, multiple samples may be run within a short time frame (most target plates contain 384 sample spots). Further, the method is sensitive enough to detect even bacteria from samples containing multiple pathogens. Finally, the preparation necessary for samples is minimal compared to other methods in use and is able to significantly diminish the time required for testing, shortening the period by 2-3 days. Variation in sample preparation (culture conditions, culture time) does not impact microbial identification using MALDI-TOF, thus ensuring the reliability of results.

Differential growth plates and differential growth panels operate according to the same principles, but differential growth plates differ in their use of selective or differential media in the solid phase. Each plate is streaked with a sample, incubated under conditions suitable for microbial growth and colony formation is assessed. Methods of this disclosure utilizing differential growth plates differ from currently employed purity plate workflows in that colony growth is not assessed visually after an overnight incubation, but using imaging techniques that reveal colony growth before it is visible to the naked eye (e.g., fewer than 6 hours, 7 hours, 8 hours, 10 hours, 12 hours). These techniques include, without limitation, light microscopy, near-field imaging and/or autofluorescence. Images of the differential growth plates are taken and mono-vs. polymicrobial calls may be made based on image variables such as optical density and/or by comparison to a library of monomicrobial and/or polymicrobial standards.

Figure 3A:
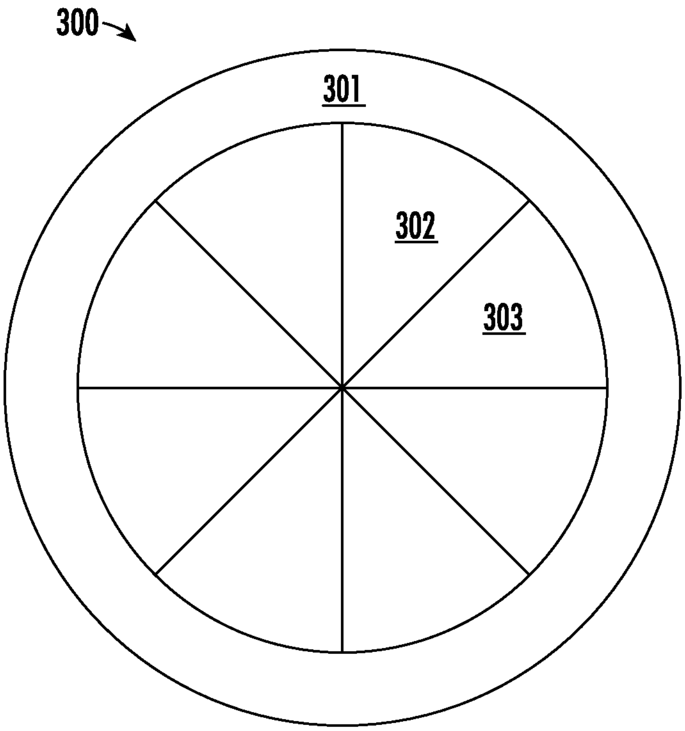
FIG. 3 shows exemplary solid-phase purity plate designs according to certain embodiments of this disclosure.
Figure 3B:
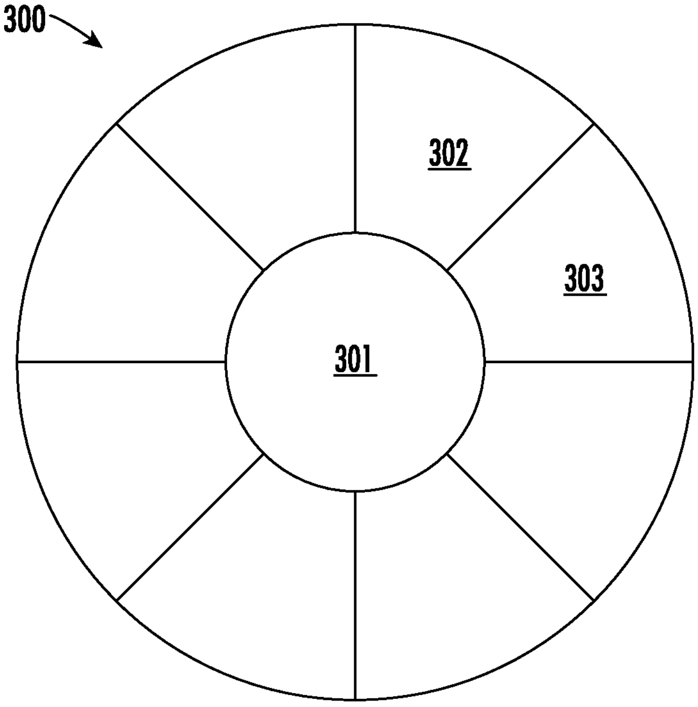

Differential growth plates may be streaked manually or using automated streakers. In some cases, it may be useful to streak multiple differential growth plates using different sample concentrations FIG. 3 depicts exemplary differential growth plates 300 according to embodiments of this disclosure. A non-selective medium 301 such as tryptic soy agar with 5% lysed blood may be located on a central or peripheral portion of the plate 300, and selective media 302, 303, etc. may be arranged radially along the plate.

Microbial ID data generated using the methods and systems described above may be used to flag polymicrobial samples. In some embodiments, ID data may be used to assist the interpretation of AST results.

In some embodiments, a single cassette comprises both a differential growth panel as described above and an AST panel, in which a plurality of wells comprise multiple antimicrobial agents, with varying concentrations in each well. Cassettes, AST panels, and automated AST systems utilizing them are described in commonly assigned US pre-grant publication no. 2018/0088141, which is incorporated by reference for all purposes.

Figure 4:
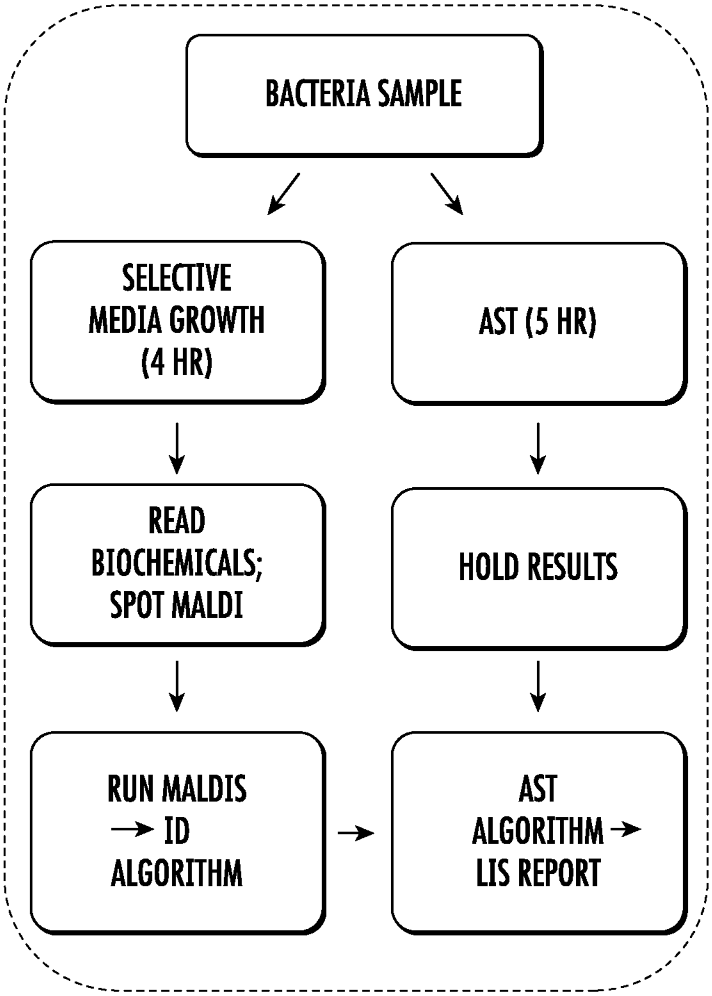
FIG. 4 shows exemplary workflow integration with AST according to certain embodiments of this disclosure.

An example showing the use of the methods described herein in parallel with rapid AST is shown in FIG. 4. The incubation times shown in the figure are exemplary of the speed of a rapid AST platform but are not intended to be limiting. In the illustrated case, the polymicrobial ID results return a definitive ID, which is then reported to the AST algorithm to enable quantitative AST results, as well as qualitative interpretive criteria, to be determined and reported to the clinic. This case further illustrates the use of automated processing, enabled by system integration of multiple modules, such as rapid AST, MALDI, fluid, and sample handling.

Rapid AST methods according to certain embodiments of the present disclosure involve the following steps: first, inoculating a microbe-containing sample onto an AST test panel that includes a plurality of reservoirs, including (a) at least one reservoir that does not include an antimicrobial, (i.e., a growth control reservoir), and (b) at least one test reservoir that includes a reagent that differentially affects the growth of a microbe depending on its anionic surface charge—e.g., a reagent that reduces the growth of a microbe with a higher anionic charge relative to a microbe with a lower anionic surface charge.

The test panel also typically includes a plurality of reservoirs that define dilution series for a plurality of antimicrobials, and AST methods of this disclosure generally involve assessing microbial growth in each antimicrobial across the dilution series to determine a minimum inhibitory concentration and, optionally, a breakpoint concentration for each antimicrobial. Before microbial growth is assessed for the antimicrobial dilution series, the test panel is incubated for a period of time under conditions appropriate for microbial growth, e.g., at a temperature (in Celsius) of 25°, 30°, 35°, 37°, etc., optionally agitated during at least a portion of the incubation period. Following incubation, microbial growth is assessed in at least one growth control reservoir. If growth meets or exceeds a predetermined minimum level, one or more endpoint assays are performed to assess the level of microbial growth in each antimicrobial at each tested concentration. These results are then evaluated, manually or algorithmically, to identify a antimicrobials to which the sample is susceptible, along with minimum inhibitory concentrations thereof.

MALDI-TOF

Samples for MALDI-TOF may be prepared using commercially available MALDI target plates and matrix solutions. In a general sample prep, a liquid comprising a suitable MALDI matrix is combined with an appropriate solvent and a microbial sample to form a liquid MALDI sample. The MALDI sample is applied to (e.g., spotted onto) a MALDI target plate which is optionally dried (e.g., by solvent evaporation) before being placed into a dedicated MALDI TOF mass spectrometer. Alternatively, the liquid microbial sample may be spotted on the MALDI target plate and allowed to dry prior to the addition of the liquid comprising the suitable MALDI matrix. Alternatively, the microbial sample may be smeared onto the target plate. An optional extraction step may be performed on the spotted microorganisms as known to those skilled in the art. A mass spectrum is generated and compared against a database of reference spectra and an ID call is made.

Microbial samples may comprise intact microbes, lysed microbes, or microbial components such as precipitated or isolated microbial proteins, lipids, glycolipids, glycoproteins, etc. In some instances, the microbial sample is processed, e.g., by the addition of a biochemical substrate, an antibody, aptamer, antisense oligonucleotide, or other reporting or detection reagent that is indicative of the presence or absence of a species or strain of microbe in a sample.

Intact microbes may be provided in the solid phase, e.g., as a single microbial colony picked from a plate, or in the liquid phase, e.g., as a liquid culture of a microbial colony or as a liquid culture obtained from a patient sample. Microbial lysis may be performed after spotting on the target, such as with formic acid, or prior to spotting on the target. Microbial components may be provided according to art-known methods such as lysis and ethanol precipitation of proteins.

MALDI-TOF analyses may be performed using custom-built or commercially available instruments, such as those sold by Bruker Daltonics (MALDI Biotyper™), bioMerieux (VITEK™ MS), Shimadzu, Waters Corporation, and others. Databases of standard mass spectra for microbial ID are also commercially available from Andromas, bioMeriux (SARAMIS) and others, and open-source or public databases are also available, e.g., mMASS, Mass-Up, pkDACLASS, MALDIquant, SpectraBank, etc. Alternatively or additionally, custom mass spectra databases may be used for ID from sample spectra.

Suitable MALDI-TOF matrices for microbial ID may include, without limitation, α-Cyano-4-hydroxycinnamic acid (HCCA), 2,5-Dihydroxybenzoic acid (DHB), 2,5-Dihydroxyacetophenone (DHAP), Sinapinic acid, 3-Hydroxypicolinic acid and mixtures thereof. A number of solvents may be suitable with these matrices, including water, ethanol, acetonitrile, trifluoroacetic acid and mixtures thereof.

MALDI-TOF sample preparation and spectrometry may be performed manually, or using automated systems such as those sold by Copan and others.

Microorganisms

An infection can include any infectious agent of a microbial origin, e.g., a bacterium, a fungal cell, an archaeon, and a protozoan. In some examples, the infectious agent is a bacterium, e.g., a gram-positive bacterium, a gram-negative bacterium, and an atypical bacterium. An antimicrobial resistant microorganism can be a microorganism that is resistant to an antimicrobial, i.e., anti-bacterial drugs, anti-fungal drugs, anti-archaea medications, and anti-protozoan drugs.

The microorganisms (e.g., a liquid suspension of microorganisms) may include one strain of microorganism. The microorganisms may include one species of microorganism. The microorganisms may include more than one strain of microorganism. The microorganisms may include one order of microorganism. The microorganisms may include one class of microorganism. The microorganisms may include one family of microorganism. The microorganisms may include one kingdom of microorganism.

The microorganisms (e.g., a liquid suspension of microorganisms) may include more than one strain of microorganism. The microorganisms may include more than one species of microorganism. The microorganisms may include more than one genus of microorganism. The microorganisms may include more than one order of microorganism. The microorganisms may include more than one class of microorganism. The microorganisms may include more than one family of microorganism. The microorganisms may include more than one kingdom of microorganism.

The microorganism may be a bacterium. Examples of bacterium include, but are not limited to, *Acetobacter aurantius, Acinetobacter bitumen, Acinetobacter* spp., *Actinomyces israelii, Actinomyces* spp., *Aerococcus* spp., *Agrobacterium radiobacter, Agrobacterium tumefaciens, Anaplasma, Anaplasma phagocytophilum, Azorhizobium caulinodans, Azotobacter vinelandii, Bacillus, Bacillus anthracis, Bacillus brevis, Bacillus cereus, Bacillus fusiformis, Bacillus licheniformis, Bacillus megaterium, Bacillus mycoides, Bacillus* spp., *Bacillus stearothermophilus, Bacillus subtilis, Bacillus Thuringiensis, Bacteroides, Bacteroides fragilis, Bacteroides gingivalis, Bacteroides melaninogenicus* (also known as *Prevotella melaninogenica*), *Bartonella, Bartonella henselae, Bartonella quintana, Bartonella* spp., *Bordetella, Bordetella bronchiseptica, Bordetella pertussis, Bordetella* spp., *Borrelia burgdorferi, Brucella, Brucella abortus, Brucella melitensis, Brucella* spp., *Brucella suis, Burkholderia, Burkholderia cepacia, Burkholderia mallei, Burkholderia pseudomallei, Calymmatobacterium granulomatis, Campylobacter, Campylobacter coli, Campylobacter fetus, Campylobacter jejuni, Campylobacter pylori, Campylobacter* spp., *Chlamydia, Chlamydia* spp., *Chlamydia trachomatis, Chlamydophila, Chlamydophila pneumoniae* (previously called *Chlamydia pneumoniae*), *Chlamydophila psittaci* (previously called *Chlamydia psittaci*), *Chlamydophila* spp., *Clostridium, Clostridium botulinum, Clostridium difficile, Clostridium perfringens* (previously called *Clostridium welchii*), *Clostridium* spp., *Clostridium tetani, Corynebacterium, Corynebacterium diphtheriae, Corynebacterium fusiforme, Corynebacterium* spp., *Coxiella burnetii, Ehrlichia chaffeensis, Ehrlichia* spp., *Enterobacter cloacae, Enterobacter* spp., *Enterococcus, Enterococcus avium, Enterococcus durans, Enterococcus faecalis, Enterococcus faecium, Enterococcus galllinarum, Enterococcus maloratus, Enterococcus* spp., *Escherichia coli, Francisella* spp., *Francisella tularensis, Fusobacterium nucleatum, Gardenerella* spp., *Gardnerella vaginalis, Haemophilius* spp., *Haemophilus, Haemophilus ducreyi, Haemophilus influenzae, Haemophilus parainfluenzae, Haemophilus pertussis, Haemophilus vaginalis, Helicobacter pylori, Helicobacter* spp., *Klebsiella pneumoniae, Klebsiella* spp., *Lactobacillus, Lactobacillus acidophilus, Lactobacillus bulgaricus, Lactobacillus casei, Lactobacillus* spp., *Lactococcus lactis, Legionella pneumophila, Legionella* spp., *Leptospira* spp., *Listeria monocytogenes, Listeria* spp., *Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium* spp., *Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma* spp., *Neisseria, Neisseria gonorrhoeae, Neis-*

*seria meningitidis, Neisseria* spp., *Nocardia* spp., *Pasteurella, Pasteurella multocida, Pasteurella* spp., *Pasteurella tularensis, Peptostreptococcus, Porphyromonas gingivalis, Prevotella melaninogenica* (previously called *Bacteroides melaninogenicus*), *Proteus* spp., *Pseudomonas aeruginosa, Pseudomonas* spp., *Rhizobium radiobacter, Rickettsia, Rickettsia prowazekii, Rickettsia psittaci, Rickettsia quintana, Rickettsia rickettsii, Rickettsia* spp., *Rickettsia trachomae, Rochalimaea, Rochalimaea henselae, Rochalimaea quintana, Rothia dentocariosa, Salmonella, Salmonella enteritidis, Salmonella* spp., *Salmonella typhi, Salmonella typhimurium, Serratia marcescens, Shigella dysenteriae, Shigella* spp., *Spirillum volutans, Staphylococcus, Staphylococcus aureus, Staphylococcus epidermidis, Staphylococcus* spp., *Stenotrophomonas maltophilia, Stenotrophomonas* spp., *Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus* spp., *Treponema, Treponema denticola, Treponema pallidum, Treponema* spp., *Ureaplasma* spp., *Vibrio, Vibrio cholerae, Vibrio comma, Vibrio parahaemolyticus, Vibrio* spp., *Vibrio vulnificus, viridans streptococci, Wolbachia, Yersinia, Yersinia enterocolitica, Yersinia pestis, Yersinia pseudotuberculosis*, and *Yersinia* spp.

The microorganism may be a fungus. Examples of fungi include, but are not limited to, *Aspergillus* spp., *Blastomyces* spp., *Candida* spp., *Cladosporium, Coccidioides* spp., *Cryptococcus* spp., *Exserohilum, fusarium, Histoplasma* spp., *Issatchenkia* spp., mucormycetes, *Pneumocystis* spp., ringworm, scedosporium, *Sporothrix*, and *Stachybotrys* spp. The microorganism may be a protozoan. Examples of protozoans include, but are not limited to, *Entamoeba histolytica, Plasmodium* spp., *Giardia lamblia*, and *Trypanosoma brucei*.

Antimicrobials

When the microorganism is a bacterium, exemplary antimicrobials include Amikacin, Aminoglycoside, Aminoglycoside amoxicillin, Aminoglycosides, Amoxicillin, Amoxicillin/clavulanate, Ampicillin, Ampicillin/sulbactam, Antitoxin, Arsphenamine, Azithromycin, Azlocillin, Aztreonam, β-lactam, Bacitracin, Capreomycin, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftaroline, Ceftaroline fosamil, Ceftazidime, Ceftibuten, Ceftizoxime, Ceftobiprole, Ceftriaxone, Cefuroxime, Cephalosporin, Chloramphenicol, Chloramphenicol(Bs), Ciprofloxacin, Clarithromycin, Clindamycin, Clofazimine, Cloxacillin, Colistin, Co-trimoxazole, Cycloserine, Dalbavancin, Dapsone, Daptomycin, Demeclocycline, Dicloxacillin, Dirithromycin, Doripenem, Doxycycline, Enoxacin, Ertapenem, Erythromycin, Ethambutol, Ethambutol(Bs), Ethionamide, Flucloxacillin, Fluoroquinolone, Fluoroquinolones, Fosfomycin, Furazolidone, Fusidic acid, Gatifloxacin, Geldanamycin, Gemifloxacin, Gentamicin, Grepafloxacin, Herbimycin, Imipenem/Cilastatin, Isoniazid, Kanamycin, Levofloxacin, Lincomycin, Linezolid, Lomefloxacin, Loracarbef, Lysostaphin, Macrolides, Mafenide, Meropenem, Methicillin, Metronidazole, Mezlocillin, Minocycline, Moxifloxacin, Mupirocin, Nafcillin, Nafcillin, Nalidixic acid, Neomycin, Netilmicin, Nitrofurantoin(Bs), Norfloxacin, Ofloxacin, Optochin, Oritavancin, Oxacillin, Oxytetracycline, Paromomycin, Penicillin, Penicillin G, Penicillin V, Piperacillin, Piperacillin/tazobactam, Platensimycin, Polymyxin B, Posizolid, Pyrazinamide, Quinupristin/Dalfopristin, Radezolid, Raxibacumab, Rifabutin, Rifampicin, Rifampin, Rifapentine, Rifaximin, Roxithromycin, Silver sulfadiazine, Sparfloxacin, Spectinomycin, Spectinomycin(Bs), Spiramycin, Streptogramins, Streptomycin, Sulbactam, Sulfacetamide, Sulfadiazine, Sulfadimethoxine, Sulfamethizole, Sulfamethoxazole, Sulfanilimide, Sulfasalazine, Sulfisoxazole, Sulfonami dochrysoidine, Tedizolid, Teicoplanin, Teixobactin, Telavancin, Telithromycin, Temafloxacin, Temocillin, Tetracycline, Thiamphenicol, ticarcillin, Ticarcillin/clavulanate, Ticarcillin/clavulanic acid, Tigecycline, Tigecycline(Bs), Tinidazole, TMP/SMX, Tobramycin, Torezolid, Trimethoprim(Bs), Trimethoprim-Sulfamethoxazole, Troleandomycin, Trovafloxacin, Vancomycin, and generics thereof or a variant thereof.

Antimicrobials whose interactions with the microorganism affect and are affected by the negative charges on the microorganism surface can include: polycationic aminoglycosides, which upon binding the cell surface displace $Mg^{2+}$ ions, which bridge lipid membrane components, thereby disrupting the outer membrane and enhancing drug uptake; cationic polymyxins (colistin and polymyxin B), whose binding to the microorganism cell is also dependent on the membrane's negative charge and for which both mutational and plasmid-mediated resistance occurs by reducing membrane negative charge; and daptomycin, a lipopeptide that resembles host innate immune response cationic antimicrobial peptides and requires $Ca^{2+}$ and phosphatidyl glycerol for its membrane-disrupting mechanism of action and for which resistance can also involve alteration in cell surface charge.

When the microorganism is a fungus, exemplary antimicrobials include 5-fluorocytosine, Abafungin, Albaconazole, Allylamines, Amphotericin B, Ancobon, Anidulafungin, Azole, Balsam of Peru, Benzoic acid, Bifonazole, Butoconazole, Candicidin, Caspofungin, Ciclopirox, Clotrimazole, Cresemba, Crystal violet, Diflucan, Echinocandins, Econazole, Efinaconazole, Epoxiconazole, Fenticonazole, Filipin, Fluconazole, Flucytosine, Grifulvin V, Griseofulvin, Gris-Peg, Haloprogin, Hamycin, Imidazoles, Isavuconazole, isavuconazonium, Isoconazole, Itraconazole, Ketoconazole, Lamisil, Luliconazole, Micafungin, Miconazole, Natamycin, Noxafil, Nystatin, Omoconazole, Onmel, Oravig, Oxiconazole, Posaconazole, Propiconazole, Ravuconazole, Rimocidin, Sertaconazole, Sporanox, Sulconazole, Terbinafine, Terconazole, Thiazoles, Thiocarbamate antifungal, Tioconazole, Tolnaftate, Triazoles, Undecylenic acid, Vfend, Voriconazole, and generics thereof or a variant thereof.

When the microorganism is a protozoan, exemplary antimicrobials include 8-Aminoquinoline, Acetarsol, Agents against amoebozoa, Ailanthone, Amodiaquine, Amphotericin B, Amprolium, Antitrichomonal agent, Aplasmomycin, Arsthinol, Artelinic acid, Artemether, Artemether/lumefantrine, Artemisinin, Artemotil, Arterolane, Artesunate, Artesunate/amodiaquine, Atovaquone, Atovaquone/proguanil, Azanidazole, Azithromycin, Benznidazole, Broxyquinoline, Buparvaquone, Carbarsone, Carnidazole, Chiniofon, Chloroquine, Chlorproguanil, Chlorproguanil/dapsone, Chlorproguanil/dapsone/artesunate, Chlorquinaldol, Chromalveolate antiparasitics, Cinchona, Cipargamin, Clazuril, Clefamide, Clioquinol, Coccidiostat, Codinaeopsin, Cotrifazid, Cryptolepine, Cycloguanil, Dehydroemetine, Difetarsone, Dihydroartemisinin, Diloxanide, Diminazen, Disulfiram, Doxycycline, Eflornithine, ELQ-300, Emetine, Etofamide, Excavata antiparasitics, Fumagillin, Furazolidone, Glycobiarsol, GNF6702, Halofantrine, Hydroxychloroquine, Imidocarb, Ipronidazole, Jesuit's bark, KAF 156, Lumefantrine, Maduramicin, Mefloquine, Megazol, Meglumine antimoniate, Melarsoprol, Mepacrine, Metronidazole, Miltefosine, Neurolenin B, Nicarbazin, Nifurtimox, Nimorazole, Nitarsone, Nitidine, Nitrofural, Olivacine, Ornidazole, Oroidin, Pamaquine, Paromomycin, Pentamidine, Pentavalent antimonial, Phanquinone, Phenamidine, Piperaquine, Primaquine, Proguanil, Project 523, Propenidazole, Pyrimethamine, Pyronaridine, Quinfamide, Quinine, Ronidazole, Schedula Romana, SCYX-7158, Secnidazole, Semapimod, Sodium stibogluconate, Spiroindolone, Sulfadoxine, Sulfadoxine-Pyrimethamine, Sulfalene, Suramin, Tafenoquine, Teclozan, Tenonitrozole, Tilbroquinol, Tinidazole, Trimetrexate, Trypanocidal agent, Warburg's tincture, and generics thereof or a variant thereof.

An antimicrobial may be a drug that operates by a mechanism similar to a herein-recited drug. Other antimicrobial drugs known in the art may be used in the methods described herein.

Liquid Suspensions

The liquid may include a growth media, such as cation-adjusted Mueller Hinton broth. This media may comprise an additive, known to those skilled in the art to promote microorganism growth, and stability. In addition to different antimicrobials, different test wells may comprise an additive known to improve AST accuracy for specific antimicrobials. For example, additional sodium chloride may be added to tests comprising oxacillin and additional calcium may be added to tests comprising daptomycin.

Biological Samples

The microorganisms described herein may be derived from biological samples. In some embodiments, the biological sample is any sample that comprises a microorganism, e.g., a bacterium and a fungal cell. The biological sample may be derived from a clinical sample.

Exemplary biological samples can include, but are not limited to, whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, nasal swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. The ordinary-skilled artisan may also appreciate that isolates, extracts, or materials obtained from any of the above exemplary biological samples are also within the scope of the present invention.

Microorganisms obtained from a biological sample may be cultured or otherwise processed as is routinely performed in the art.

Controls Used in AST Methods

Controls may include antimicrobials for which the microorganism is not susceptible. As examples, if the assay is used to determine the susceptibility of gram-positive bacteria, then the controls (and the test incubations) may include one or more antimicrobials that target gram-negative bacteria, and if the assay is used to determine the susceptibility of eukaryotic microorganisms, the control (and the test incubations) may include one or more antibacterial antimicrobials.

In some embodiments, the control is a positive control measured from microorganisms under otherwise identical conditions but without antimicrobials or with one or more antimicrobials for which the microorganisms are not susceptible. In some embodiments, the control is measured from microorganisms under otherwise identical conditions but without nutrients. In some embodiments, the control is measured from microorganisms under otherwise identical conditions with one or more toxins known to inhibit growth of the microorganisms.

Controls may be historic controls. In some embodiments, the test incubations are performed after control incubations have been performed. In some embodiments, controls are performed in a cartridge distinct from the cartridge comprising the test incubations.

Cartridges

A cartridge can be a container that is capable of holding and allowing growth of a liquid suspension of microorganisms. Non-limiting examples of a cartridge can include a culture flask, a culture dish, a petri dish, a bioassay dish, a culture tube, a test tube, a microfuge tube, a bottle, a microchamber plate, a multi-chamber plate, a microtiter plate, a microplate. The cartridge may comprise one chamber. The cartridge may include a plurality of chambers, each chamber being a space capable of holding a liquid suspension in physical isolation from another space; an example of a chamber is a chamber in a multiwall plate. The cartridge may comprise 1, 2, 3, 4, 5, 6, 7, 8, 9, 10, 11, 12, 24, 48, 96, 192, 384, 1536, or more chambers, and any number of chambers in between. The bottom of the cartridge chamber may be flat, round, or V-shaped.

Antimicrobials present within a plurality of chambers on the cartridge can be suspended in a medium. In some embodiments, the antimicrobial is present in the form of antimicrobial film. In certain embodiments, the antimicrobial is in solid form. In some embodiments, the solid antimicrobial is lyophilized and/or dried. Certain embodiments provide for one or more antimicrobials present in one or more cartridge chambers as antimicrobial films, in solid form, lyophilized, or dried prior to introduction of a suspension of microorganisms.

An antimicrobial dilution series may be frozen, lyophilized, or prepared fresh prior to plate inoculation with a sample. In some cases, inoculation of cartridges can be performed either by hand or using an automated system. In some examples, such as in cases of fresh antimicrobial plates, an automated liquid handling system may be used to prepare the cartridge with antimicrobial dilution series. Inoculation processes can include any of various processes that may be known in the art.

As described herein, cartridges can be used to contain various combinations of fluids in order to carry out multiple testing sequences, such as a check point assay and a plurality of different growth assays. In some embodiments, a cartridge has a set of chambers used to facilitate the one or more checkpoint assays and a set of chambers used to facilitate the one or more growth assays. By way of example, a cartridge can include an array of chambers arranged in rows and columns. The cartridge can include a set of control chambers and a set of antimicrobial testing chambers. The set of control chambers can include two chambers and the set of testing chambers can include the remainder of chambers along the plate. In some embodiments, the set of control chambers includes at least two chambers, where one chamber is a growth chamber and another chamber is a no-growth chamber. In some embodiments, the growth chamber includes, or be inoculated to include, a combination of broth and a patient sample such that the microorganisms in the patient sample can grow within the broth during an incubation period. In certain embodiments, antimicrobials are not added to the checkpoint assay chamber. Whereas, in some embodiments, the no-growth chamber can include, or be inoculated to include, broth without the patient sample (i.e., broth in the absence of the microorganisms from the patient sample). In some embodiments, antimicrobials are also not added to the no-growth chamber. Thus, during an incubation period, the no-growth chamber can serve as a baseline as compared to the growth chamber in which the microorganisms can grow.

In some embodiments, each cartridge includes a "test panel," a plurality of antimicrobials distributed across multiple wells in a defined dilution series for each antimicrobial (e.g., a 2-fold dilution series, a 10-fold dilution series, etc.). In addition, each cartridge or test panel can contain control chambers, such as a growth control chamber, a no growth (contamination) control chamber and/or a saline control chamber. The saline control chamber can represent FIT control approximately equal to the initial concentration of microorganism in inoculum. The cartridges can include multiple chambers (e.g., 96 chamber cartridge or 384 chamber cartridge) with a cover (e.g., a removable lid) and an identifier (e.g., a bar code) that uniquely defines antibiotic configuration and a unique code, which defines the plate and can be associated with a unique patient sample conforming to HIPAA.

The testing chambers can include any of various combinations of the patient sample and various types and concentrations of antimicrobials for which susceptibility can be analyzed. Rows of chambers can be dedicated to a particular antimicrobial and concentrations of that antimicrobial can vary between columns of the same row. For example, a cartridge can have a row of chambers containing penicillin where each chamber from left to right contains an increasing concentration of penicillin.

Of course, other examples are possible. For example, the different chambers and sets of chambers can be positioned at any of various locations along a cartridge. Additionally, the different sets of chambers (e.g., control chambers and testing chambers) can include greater or fewer individual chambers along the cartridge. Additionally, in some cases, not all chambers are used/occupied during testing.

Automated AST Methods

The methods described herein can be performed in an automated manner using commercially available equipment, custom made equipment, or a combination thereof. Automating the methods allows for performance of a greater number of assays as well as increased consistency among assays. Automation can also increase speed and resolution of these methods. Automated AST methods are described, for example, in US Pub. 2019/0212339 which is hereby incorporated by reference.

Surface-Binding Probe Assays

Surface-binding assays (also referred to as surface-binding probe assays) can utilize a signaling agent. Signaling agents typically comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary enzymes include horseradish peroxidase, alkaline phosphatase, acetyl cholinesterase, glucose oxidase, beta-D-galactosidase, beta-lactamase, and a combination thereof.

A signal generator may include one or more chemical moieties conjugated to one or more microorganism receptors. Signal generators include, but are not limited to, one or more catalysts (including enzymes, metal-oxide nanoparticles, organometallic catalysts, nanoparticles designed for signal amplification (such as those described in the U.S. Provisional Applications to which the present application claims priority and incorporates by reference in their entireties), bacteriophages comprising signal generating elements, fluorophores (including organic fluorophores, europium, or ruthenium(II), rhenium(I), palladium(II), platinum(II)-containing organometallics), and/or colorimetric dyes (including organic stains). Combinations of the above may be used, such as nanoparticles, dendrimers, and/or other nanoscale structures with enzymes, fluorophores, and/or organometallic molecules.

The chemical moiety may be conjugated to a signaling agent before contacting the signaling agent to a microorganism, while the signaling agent is initially contacted to a microorganism, or after the signaling agent has contacted a microorganism.

When the signaling agents are added to AST dilutions containing a microorganism, signaling agent receptors (e.g., moieties that can bind specifically or non-specifically to a microorganism) may associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are free in solution, as defined by those not bound to intact bacteria. Note that free signaling agents may be bound to soluble microbial components if, for example, microorganisms lyse in response to antimicrobial treatment.

The number of signaling agents that associate with and/or intercalate into microorganism surfaces is proportional to the microorganism surface area. Microorganism surface area is strongly associated with truly resistant microorganisms. In particular, in the case of microorganisms that swell or elongate in response to MIC- and sub-MIC concentrations of antimicrobials (e.g., filament forming bacteria), metabolic and/or volumetric identifications are known to give false susceptibility profiles for rapid AST time points, defined as those less than six hours. To overcome this limitation, the present invention translates microorganism surface area (rather than volume) into a measurable signal such as an optical signal. The methods described herein are able to accurately determine microorganism resistance profiles in less than six hours.

In order to separate signaling agents associated with and/or intercalated into microorganisms from free signaling agents, it may be necessary to perform one or more separation and/or competitive binding steps. Such steps include, but are not limited to, centrifugation (e.g., with a g-force>500×g), filtration (e.g., via a filter having pores smaller than or equal to 0.45 microns, or smaller than or equal to 0.2 microns), electrophoresis, and/or magnetic capture; such steps are well-known to those skilled in the art.

In order to promote signaling agent binding and/or reduce background, it may further be advantageous, before adding signaling agents, to separate microorganisms from the liquid in which they were suspended during incubation. Such separations may include but are not limited to, centrifugation, filtration, electrophoresis, and/or magnetic capture.

Signaling agents may be added together with microorganisms and/or antimicrobials, such that they are present for the entire AST incubation period. This total period may be up to twenty-four hours, or within eight hours, or within five hours. Alternatively, signaling agents may be added to microorganisms and antimicrobial after a prescribed incubation period. This period may be up to twenty-four hours, or within eight hours, or within four hours.

Signaling agents are designed to associate with and/or intercalate in microorganism surfaces, including walls and/or membranes. Signaling agents designed for association comprise binding moieties including, but are not limited to, one or more antibodies, lectins, other proteins, small molecules with one or more charged chemical groups, small molecules with one or more functional chemical groups, phages, glycoproteins, peptides, aptamers, charged small molecules, small molecules with fixed charges, charged polymers, charged polymers with fixed charges, hydrophobic small molecules, charged peptide, charged peptides with fixed charges, peptides with alternating hydrophilic and hydrophobic regions, and/or small molecule ligands, which may or may not be organometallic complexes. Molecules designed for microorganism association are well-known to those skilled in the art. Signaling agents may remain bound to microorganisms and/or may be internalized, thus all associations are included. Signaling agents designed for intercalation may include, but are not limited to, small hydrophobic molecules, hydrophobic peptides, and/or peptides with alternating hydrophobic and hydrophilic regions. Molecules designed for microorganism intercalation are well-known to those skilled in the art. Signaling agents may further be specific to one or more types of microorganisms. Signaling agents may have multiple receptors. These may enhance binding and/or enable simultaneous binding to two or more microorganisms, which may further serve to agglutinate bacteria. Prior to or concurrently with the addition of signaling agents it may be advantageous to adjust the solution pH. This may be beneficial for enhancing charge-charge interactions between microorganisms and signaling agents. The anionic charge of microorganisms may be increased by titrating the solution pH above neutral (more basic). It may thus be beneficial to utilize moieties with one or more fixed, cationic charges.

It is noteworthy that the signaling agent may specifically bind to a microorganism (e.g., an antibody that specifically binds to a microorganism species or a strain of microorganism) or my non-specifically binds to a microorganism (e.g., by a generic covalent or non-covalent bond formation and another non-specific chemical association known in the art).

Alternately, chemicals and/or biochemicals which are capable of associating with signaling agents may be added to the liquid in which the microorganisms are suspended during growth, such that chemicals and/or biochemicals are incorporated into microorganisms during incubation. This may serve to enhance signaling agent association with microorganisms. In alternative embodiments, the signaling agents themselves may be present in the liquid in which the microorganisms are suspended during incubation and may be incorporated into microorganisms during growth.

The signaling agents can comprise an amplifier signal generator (amplifier group), such that the signal from each intact microorganism may be amplified beyond the number of signaling agents associated with each microorganism. For example, the enzyme horseradish peroxidase (HRP) is known to be able to amplify signals>$1\times10^4$-fold. Thus, if one hundred HRP molecules are bound to each microorganism surface, an amplification of $10^6$ may be achieved. This may increase the speed with which AST determinations may be made by enabling discrimination of microorganism concentrations that cannot otherwise be differentiated. Use of Europium formulations similarly provides signal amplification.

Alternatively, the signaling agents may comprise optical dye precursors known to those skilled in the art as membrane dyes that are designed to greatly increase fluorescence emission upon intercalation into a hydrophobic region, such as a cell membrane. Assays designed with these signaling agents may require microorganisms to be concentrated into a smaller volume, approaching a plane, to produce sufficient signals so as to be easily optically measured. Interfering species may require the use of near-IR fluorophores.

Exemplary amplifier groups include those described in, e.g., International Publication No. WO 2016/015027 and in International Application No. PCT/US16/42589, each of which is incorporated by reference in its entirety. An amplifier group can comprise a catalyst, a fluorophore, a colormetric dye, an enzyme, a catalyst, or a nanoparticle. Exemplary fluorophores include those described in FIG. 1, Table 1 of International Application No. PCT/US16/42589, which is incorporated by reference in its entirety. An amplifier group can comprise a lanthanide. Lanthanides include, but are not limited to, is europium, strontium, terbium, samarium, or dysprosium.

An amplifier group can comprise an organic fluorophore, e.g., a coordination complex. The coordination complex can be europium coordination complex, a ruthenium coordination complex, a rhenium coordination complex, a palladium coordination complex, a platinum coordination complex. An amplifier can comprise a chemiluminophore, a quantum dot, an enzyme, an iron coordination catalyst, a europium coordination complex, a ruthenium coordination complex, a rhenium coordination complex, a palladium coordination complex, a platinum coordination complex, a samarium coordination complex, a terbium coordination complex, or a dysprosium coordination complex.

In some embodiments, an amplifier group comprises a moiety that is:

(III)

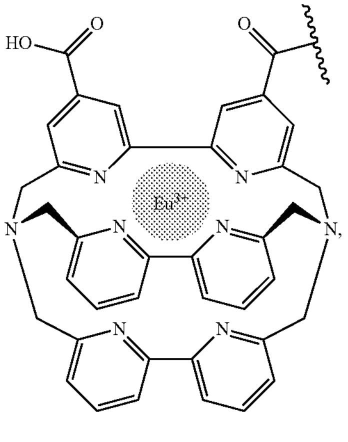

-continued
(IV)
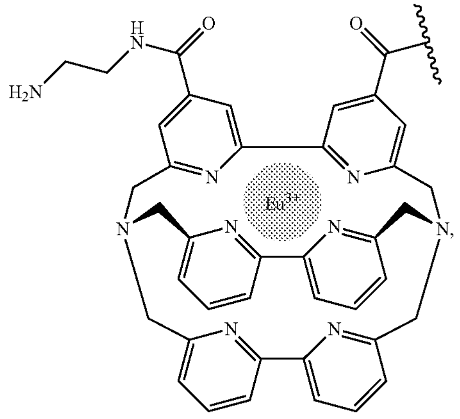
or
(V)
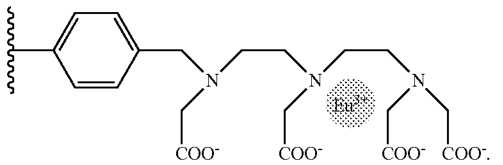
In some embodiments, an amplifier group comprises a moiety that is:
(VI)
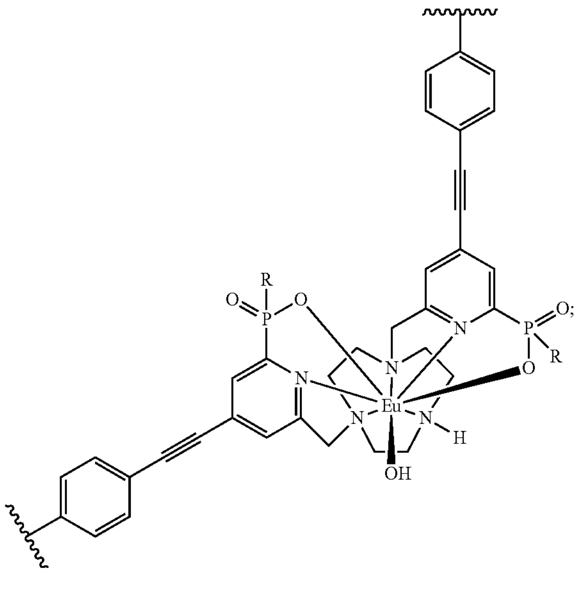
-continued
(VII)
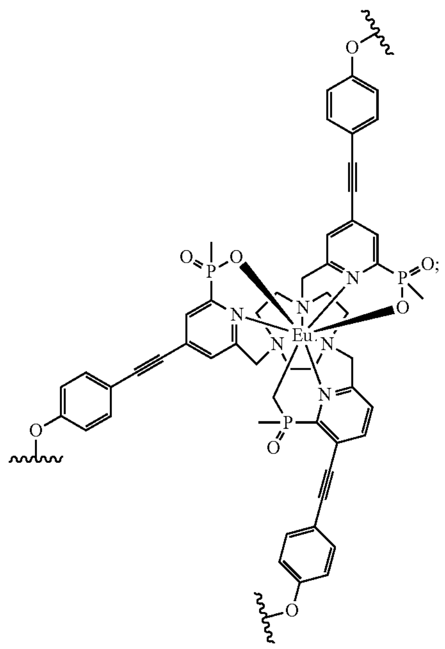
(VIII)
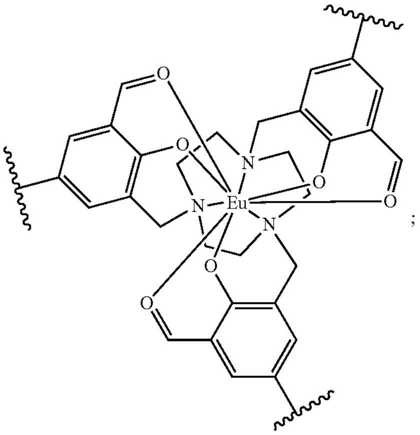
;
(IX)
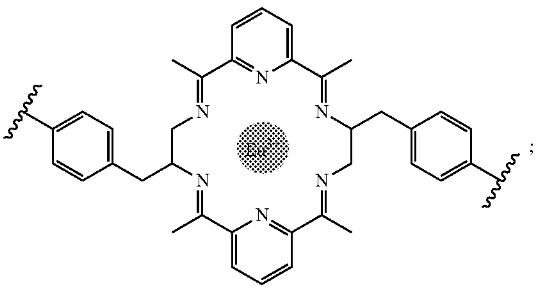
; or -continued (X)

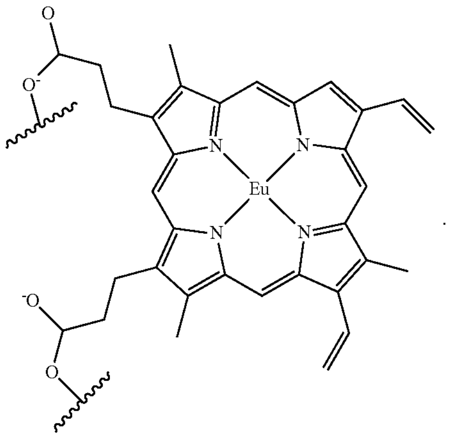

.

An amplifier group can comprise a fluorophore or colormetric dye. Suitable fluorophores and colormetric dyes are well known to those skilled in the art and are described in *The Molecular Probes Handbook. A Guide to Fluorescent Probes and Labeling Technologies,* 11$^{th}$ Ed. (2010) and Gomes, Femandes, and Lima *J. Biochem. Biophys. Methods* 65 (2005) pp 45-80, which are herein incorporated by reference in their entirety. Exemplary fluorophores also include those described in, e.g., International Publication No. WO 2016/015027 and in International Application No. PCT/US16/42589, each of which is incorporated by reference in its entirety.

Examples of suitable fluorophore or colormetric dyes include, but are not limited to, ethidium bromide, propidium iodide, SYTOX green, phenanthridines, acridines, indoles, imidazoles, cyanine, TOTO, TO-PRO, SYTO, 5-carboxy-2, 7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-ROX (carboxy-X-rhodamine), 6-Carboxyrhodamine 6G, 7-Amino-4-methylcoumarin, 7-Aminoactinomycin D (7-AAD), 7-Hydroxy-4-methylcoumarin, 9-Amino-6-chloro-2-methoxyacridine, ACMA (9-Amino-6-chloro-2-methoxyacridine), Acridines, Alexa Fluors, Alizarin, Allophycocyanin (APC), AMCA (Aminomethylcoumarin), Bodipy, Carboxy-X-rhodamine, Catecholamine, Fluorescein (FITC), Hydroxycoumarin, Lissamine Rhodamine, Monobromobimane, Oregon Green, Phycoerythrin, SYTO, Thiadicarbocyanine (DiSC3), Thioflavin, X-Rhodamine, C or TetramethylRodamineIsoThioCyanate.

An amplifier group can comprise an organometallic compound, transition metal complex, or coordination complex. Examples of such amplifier groups include, but are not limited to, those described in EP 0 180 492, EP 0 321 353, EP 0 539 435, EP 0 539 477, EP 0 569 496, EP139675, EP64484, U.S. Pat. Nos. 4,283,382, 4,565,790, 4,719,182, 4,735,907, 4,808,541, 4,927,923, 5,162,508, 5,220,012, 5,324,825, 5,346,996, 5,373,093, 5,432,101, 5,457,185, 5,512,493, 5,527,684, 5,534,622, 5,627,074, 5,696,240, 6,100,394, 6,340,744, 6,524,727, 6,717,354, 7,067,320, 7,364,597, 7,393,599, 7,456,023, 7,465,747, 7,625,930, 7,854,919, 7,910,088, 7,955,859, 7,968,904, 8,007,926, 8,012,609, 8,017,254, 8,018,145, 8,048,659, 8,067,100, 8,129,897, 8,174,001, 8,183,586, 8,193,174, 8,221,719, 8,288,763, 8,362,691, 8,383,249, 8,492,783, 8,632,753, 8,663,603, 8,722,881, 8,754,206, 8,890,402, 8,969,862, 9,012,034, 9,056,138, 9,118,028, 9,133,205, 9,187,690, 9,193,746, 9,312,496, 9,337,432, 9,343,685, 9,391,288, and 9,537,107, which are incorporated by reference in their entirety. Exemplary organometallic compounds, transition metal complexes, or coordination complexes also include those described in, e.g., International Publication No. WO 2016/015027 and in International Application No. PCT/US16/42589, each of which is incorporated by reference in its entirety.

In some embodiments, amplifier group is a lanthanide coordination complex such as a complex between a lanthanide (e.g., Eu or Tb) and a tetradentate ligand or a complex between a lanthanide (e.g., Eu or Tb) and a cryptate ligand. In some embodiments, amplifier group is a coordination complex of Lanthanum (La), Cerium (Ce), Praseodymium (Pr), Neodymium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Ruthenium (Ru), Rhodium (Rh), Palladium (Pd), Osmium (Os), Iridium (Ir), or Platinum (Pt). In some embodiments, amplifier group is a coordination complex of a rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium. In some embodiments, amplifier group is a coordination complex of a lanthanide (e.g., Europium or Terbium) with diethylenetriaminetetraacetic acid or cryptate ligand.

Specific examples of a signaling agent include, but are not limited to, moieties comprising:

(1)

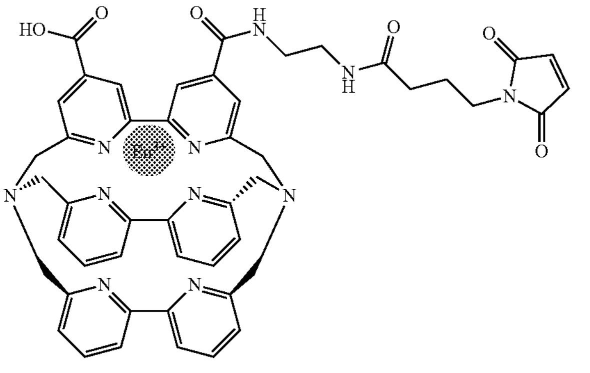

Eu-cryptate-maleimide (2)

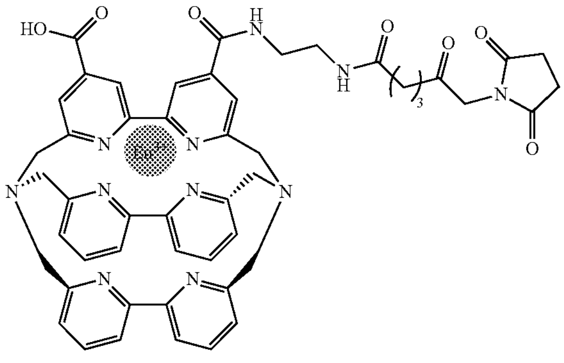

;

Eu-cryptate-NHS

-continued
(3)
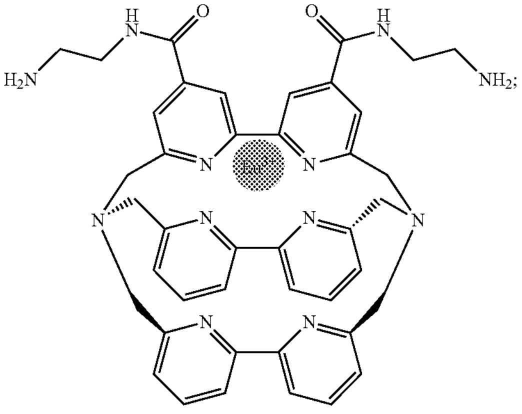
Eu-cryptate-diamine
(4)
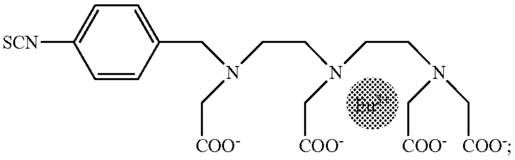
Eu-N1-ITC (Delfia)
(5)
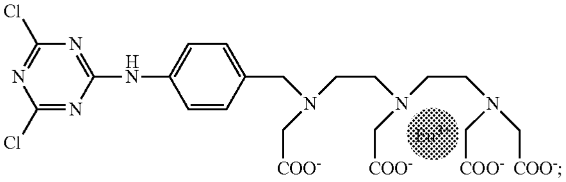
Eu-N1-DTA
(6)
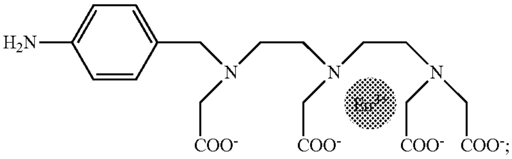
Eu-N1-amino
(7)
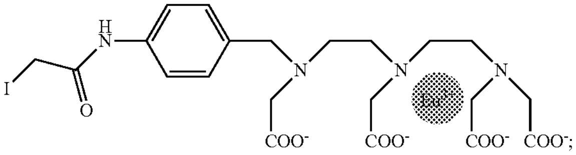
Eu-N1-iodoacetamido
(8)
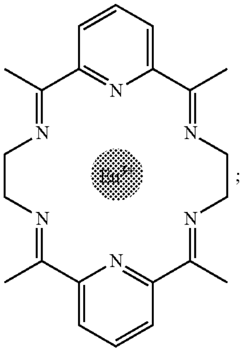
(9)
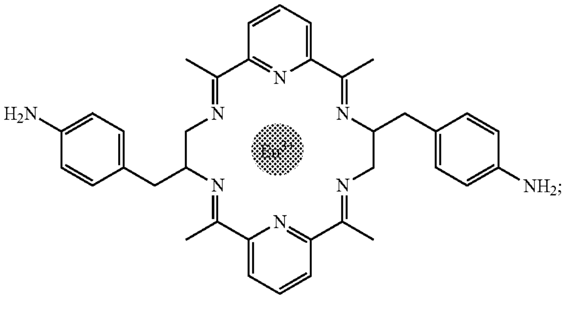
(10)
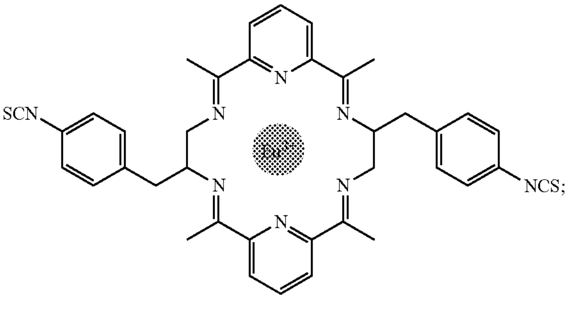

-continued (11)

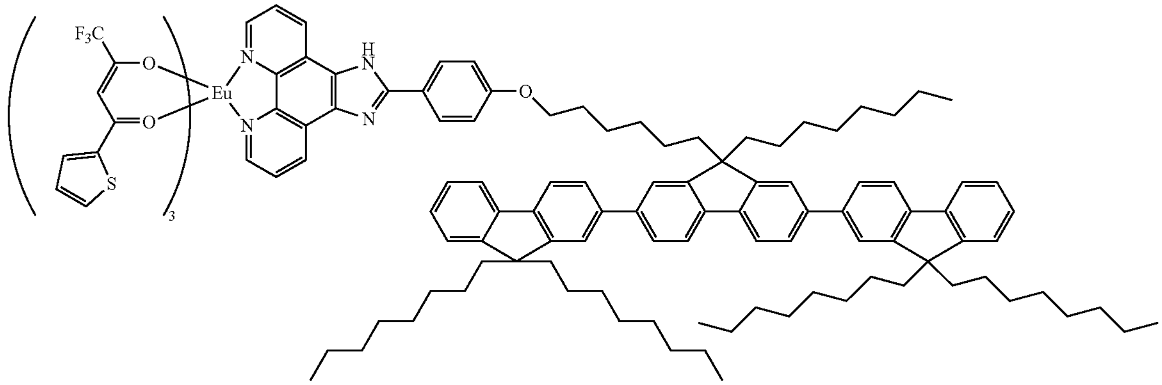

; or (12)

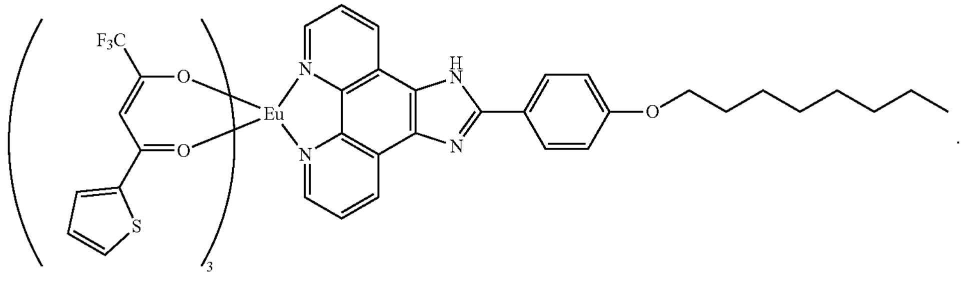

A signaling agent can comprise a luminophore (donor) which features high luminescence quantum efficiency and long luminescence decay time (>100 ns). Exemplary luminophores are cationic, metalorganic complexes of palladium, rhodium, platinum, ruthenium, osmium, rare earths (in particular, europium and lanthanum). The organic portion of these metalorganic complexes may consist, for example, of ligands from the group of porphyrins, bipyridyls, phenanthrolines or other heterocyclical compounds.

In some embodiments, a signaling agent capable of binding a microorganism surface comprises an antibody (e.g., monoclonal or polyclonal), modified antibodies (e.g., biotinylated monoclonal antibody, biotinylated polyclonal antibody, europium chelate-antibody, horseradish peroxidase-conjugated antibody), antibody variants (e.g., Fab: fragment, antigen-binding (one arm); $F(ab')_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), WGA-Biotin, PolymixinB-Biotin, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises or is formed from a structure comprising an antibody, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises an amplifier group that comprises a lanthanide coordination complex, and/or an enzyme and streptavidin and/or an antibody and/or aptamer. In some embodiments, a signaling agent capable of binding a microorganism surface comprises a binding moiety comprising a polyclonal and/or monoclonal antibody.

In some embodiments, a signaling agent capable of binding a microorganism surface comprises a binding moiety comprising a modified antibody. Exemplary modified antibodies include a biotinylated monoclonal antibody, biotinylated polyclonal antibody, a europium chelate-antibody, and a horseradish peroxidase-conjugated antibody. In some embodiments, a signaling agent capable of binding a microorganism surface comprises a binding moiety comprising an antibody variant. Exemplary antibody variants include Fab: fragment, antigen-binding (one arm); $F(ab')_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), In some embodiments, a signaling agent capable of binding a microorganism surface comprises WGA-Biotin or PolymixinB-Biotin. In some embodiments, a signaling agent capable of binding a microorganism surface comprises a binding moiety comprising a synthetic and/or natural ligand and/or peptide. In some embodiments, a ligand and/or peptide is selected from bis(zinc-dipicolylamine), TAT peptide, serine proteases, cathelicidins, cationic dextrins, cationic cyclodextrins, salicylic acid, lysine, and combinations thereof. In some embodiments, a signaling agent capable of binding a microorganism surface comprises a binding moiety comprising a synthetic and/or natural polymer and/or glycopolymer. In embodiments, a natural and/or synthetic polymer is linear or branched and selected from amylopectin, Poly(N-[3-(dimethylamino)propyl]methacrylamide), poly(ethyleneimine), poly-L-lysine, poly[2-(N,N-dimethylamino)ethyl methacrylate], and combinations thereof. In some embodiments, a natural and/or synthetic polymer and/or glycopolymer comprises moieties including, but not limited to, chitosan, gelatin, dextran, trehalose, cellulose, mannose, cationic dextrans and cyclodextrans, quaternary amines, pyridinium tribromides, histidine, lysine, cysteine, arginine, sulfoniums, phosphoniums, or combinations thereof including, but not limited to, co-block, graft, and alternating polymers. In some embodiments, a signaling agent capable of binding a microorganism surface comprises a binding moiety comprising a glycoprotein selected from mannose-binding lectin, other lectins, annexins, and combinations thereof.

In some embodiments, a signaling agent capable of binding to a microorganism surface comprises: an antibody; and a europium coordination complex. In some embodiments, a signaling agent capable of binding to a microorganism surface comprises a linker group L that comprises $NH_2$-PEG-Biotin (2K), $NH_2$-PEG-Biotin (4K), sulfo-NHS-Biotin, WGA-Biotin, or polymixinB-Biotin. In some embodiments, a signaling agent capable of binding to a microorganism surface comprises a europium complex comprises:

(III)

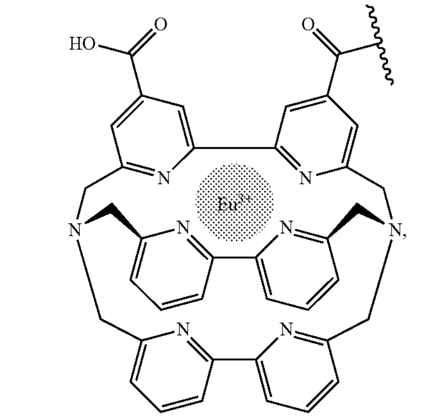

(IV)

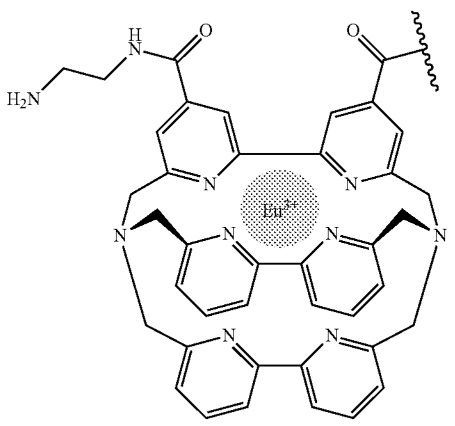

or

-continued (V)

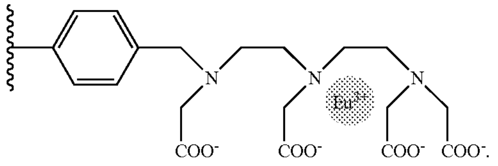

In some embodiments, a signaling agent capable of binding to a microorganism surface comprises a europium complex comprises:

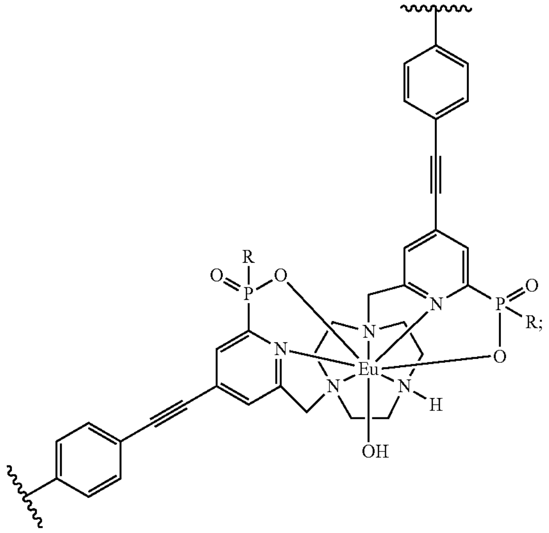

or

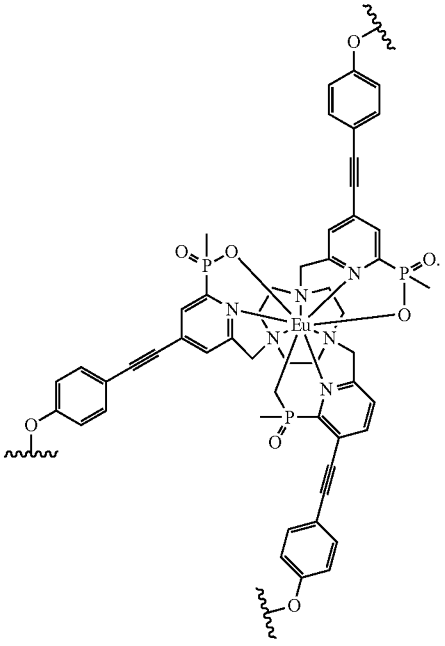

Alternatively, the signaling agents may be part of a pair, such as FRET/TR-FRET donor and acceptors or singlet oxygen pairs consisting of a photosensitizer and detector. Assays designed with these signaling agents may require the separation of the microorganisms from the initial growth media, with subsequent resuspension into a desired reaction buffer prior to the addition of the signaling reagents. Conversely, assays designed with these signaling agents may require no separation steps due to the required relative distance necessary to generate a signal.

Examples of FRET/TR-FRET donors include, but are not limited to, Lanthanide (Eu, Sm, Dy, or Tb)-containing cryptate organometallic (CisBio), Lance Eu-W1024 (Perkin Elmer), Lance Eu-W8044 (Perkin Elmer), also any organic fluorescent pair donor.

Examples of FRET/TR-FRET acceptors include, but are not limited to, matched organic dyes, such as ULight dye (Perkin Elmer), SureLight APC (Perkin Elmer), allophycocyanin, Cy5, d2 dye (CisBio), also any organic fluorescent pair acceptor.

Examples of singlet oxygen photosensitizers include, but are not limited to, methuselah Green Carboxy (Ursa Bio), Sensitizer Blue (Ursa Bio), rose Bengal, Erythrosin B, methylene blue, chlorophylls, AlphaBead donor (Perkin Elmer).

Examples of singlet oxygen detectors include, but are not limited to, singlet oxygen detector green (ThermoFisher), trans-1-(2'-methoxyvinyl)pyrene, Si-DMA (Dojindo), AlphaBead acceptor (Perkin Elmer).

Examples of incorporators include, but are not limited to, ethynyl-D-alanine (EDA), azido-D-alanine (ADA), fluorescent D-alanines described in *Angew Chem Int Ed Engl.* 2012 Dec. 7; 51(50): 12519-12523.

EXAMPLES

Example 1: Differentiation of *E. coli* and *K. pneumoniae* in Polymicrobial Cultures ATCC® samples of *E. coli* and *K. pneumoniae* were cultured on tryptic soy agar with 5% lysed sheep blood overnight at 35° C. For each species, 3-5 colonies were picked and a 0.5 McFarland inoculum was prepared in sterile saline. Five samples were made by combining the innocula according to the following table:

TABLE 3

Concentrations of *E. coli* and *K. pneumoniae* in polymicrobial cultures

| Sample | *E. coli* McFarland | *K. pneumoniae* McFarland |
|---|---|---|
| 1:1 | 500 μL | 500 μL |
| 1:3 | 250 μL | 750 μL |
| 1:10 | 90 μL | 910 μL |
| 1:30 | 32 μL | 968 μL |
| 1:100 | 10 μL | 990 μL |

For each of the 5 samples, as well as the *E. coli* and *K. pneumoniae* McFarlands as controls, 25 μL aliquots were added to each of (1) 100 μL of Mueller-Hinton broth (MHB; Becton Dickinson), (2) 100 μL of Voges-Proskauer broth (VPB; Sigma), and (3) tryptophan [or peptone] broth (TPB; Sigma) in a 96-well plate. The plate was covered and incubated under orbital shaking conditions at 35° C. for 3 hours.

Following the 3.5-hour initial growth, 1-napthol (Sigma) and potassium hydroxide (Sigma) were added to each VPB well and Kovac's Reagent (Sigma) was added to each TPB well. The samples were returned to the incubator for an additional 30-minute growth period.

Figure 5A:
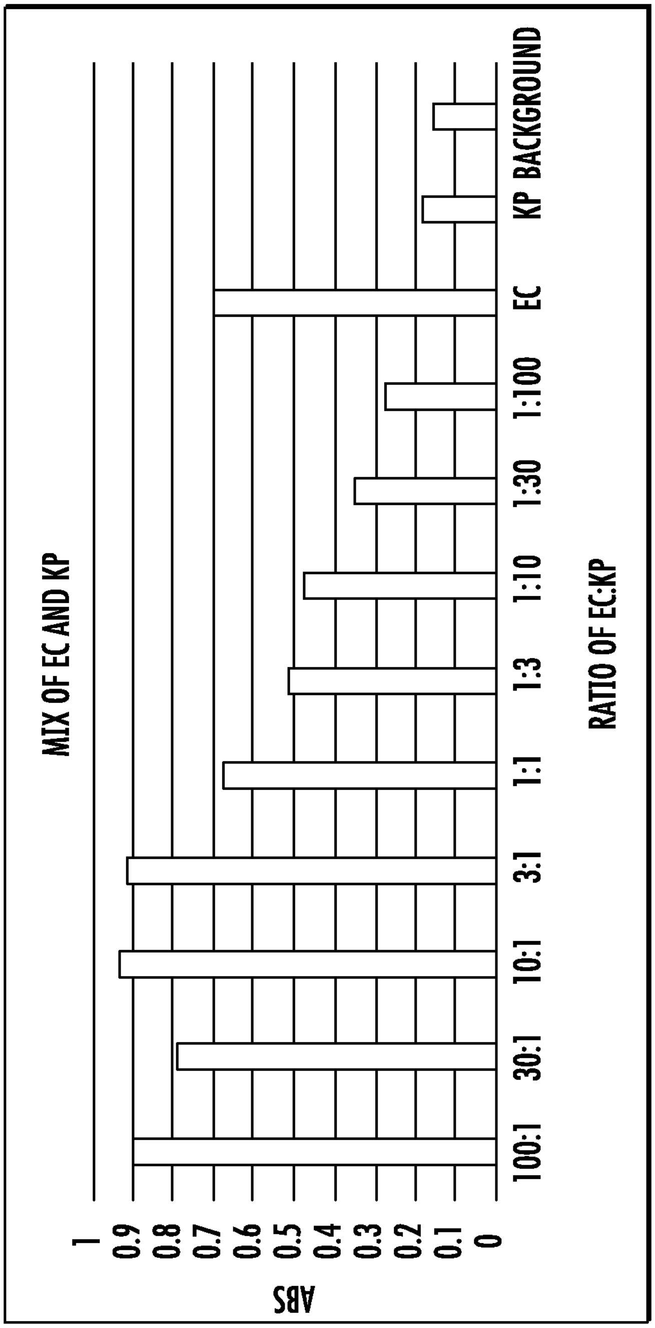
FIG. 5A shows indole test absorbance readings vs. *K. pneumoniae*-to-*E. coli* ratio for five different polymicrobial concentrations and controls.

Following the additional 30-minute growth period, the plate was removed from the incubator and the absorbance of the VPB wells and the TPB wells was read (450-650 nm). Absorbance results are presented in FIG. 5. The plates were then centrifuged at 3,500×g for 5 minutes to pellet the bacteria. Supernatants were aspirated and pellets were resuspended in 100 L of deionized water (DI) and the plates were again centrifuged at 3,500×g for 5 minutes to pellet the bacteria. The supernatants were again aspirated, followed by pellet resuspension in 4 L of DI water, and one microliter of the suspension was spotted on a Bruker Daltonics 48-sample MALDI. Formic acid (70%, 1 μL) was added after each sample is spotted followed by 1 L of a matrix consisting of cyano-4-hydroxycinnamic acid (10 mg/mL) in a solution of acetonitrile (47.5%) and trifluoroacetic acid (2.5%). MALDI-TOF mass spectra were generated according to manufacturer's instructions.

Example 2: Differentiation of Coagulase-Negative *Staphlococci* from *S. pneumoniae*

Samples of *S. lugdunensis* (clinical isolate provided by TriCore Reference Laboratories) and *S. pneumoniae* (ATCC® 49619) were cultured on tryptic soy agar with 5% lysed sheep blood overnight at 35° C. For each species, 3-5 colonies were picked and a 0.5 McFarland inoculum was prepared in sterile saline. Five samples were made by combining the innocula according to the following table:

TABLE 4

Concentration of coagulase-negative Staphlococci from *S. pneumoniae*

| Sample | *S. lugdunensis* McFarland | *S. pneumoniae* McFarland |
|---|---|---|
| 1:1 | 500 μL | 500 μL |
| 1:3 | 250 μL | 750 μL |
| 1:10 | 90 μL | 910 μL |
| 1:30 | 32 μL | 968 μL |
| 1:100 | 10 μL | 990 μL |

For each of the 5 samples, as well as the *S. lugdunensis* and *S. pneumoniae* McFarlands as controls, 25 μL aliquots were added to each of (1) 100 μL of Mueller-Hinton broth (MHB; Becton Dickinson), (2) 100 μL of mannitol salt broth (MSB; HiMedia), and (3) selective Strep broth (SSB; Hardy Diagnostics) in a 96-well plate. The plate was covered and incubated under orbital shaking conditions at 35° C. for 4 hours.

After growth was complete, samples were prepared and MALDI-TOF mass spectra were generated according to the procedure in Example 1.

Example 3: Differentiation of *E. coli* and *S. aureus* in Polymicrobial Cultures ATCC® samples of *E. coli* (25922) and *S. aureus* (29213) were cultured on tryptic soy agar with 5% lysed sheep blood overnight at 35° C. For each species, 3-5 colonies were picked and a 0.5 McFarland inoculum was prepared in sterile saline. Five samples were made by combining the McFarlands according to the following table:

TABLE 5

| Concentrations of *E. coli* and *S. aureus* in polymicrobial cultures | | |
|---|---|---|
| Sample | *E. coli* McFarland | *S. aureus* McFarland |
| 1:1 | 500 μL | 500 μL |
| 1:3 | 250 μL | 750 μL |
| 1:10 | 90 μL | 910 μL |

TABLE 5-continued

| Concentrations of *E. coli* and *S. aureus* in polymicrobial cultures | | |
|---|---|---|
| Sample | *E. coli* McFarland | *S. aureus* McFarland |
| 1:30 | 32 μL | 968 μL |
| 1:100 | 10 μL | 990 μL |

For each of the 5 samples and the *E. coli* and *S. aureus* McFarlands as controls, 25 μL aliquots are added to each of (1) 100 μL of Mueller-Hinton broth (MHB; Becton Dickinson), (2) 100 μL of mannitol salt broth (MSB; HiMedia), and (3) MacConkey broth (MCK; Sigma) in a 96-well plate. The plate was covered and incubated under orbital shaking conditions at 35° C. for 4 hours.

After growth was complete, samples were generated and MALDI-TOF mass spectra were generated according to the procedure in Example 1.

Example 4: Differentiation of Additional Co-Cultures Using MALDI-TOF

Polymicrobial mixtures were made by combining bacterial suspensions at different ratios. These suspensions were used to inoculate 100 μl media in 96-well plates in triplicate. Media included non-selective (mueller hinton broth, MHB), selective (macConkey broth, MAC; mannitol salt broth, MSB; cetrimide broth, CB; *streptococcus* enrichment broth, SEB; Leads agar plate, LP; todd hewitt broth, THB) and differential media (bromcresol purple broth, BpB, containing sucrose, Suc or arabinose, Ara). To further enhance selectivity, antibiotics lysostaphin or bacitracin were added to selective media as indicated. Inoculated plates were incubated at 37° C. in ambient air incubator for 3 to 5 hours. Cells were then pelleted by centrifugation and washed twice with deionized water before spotting 1 μl of concentrated cells on the MALDI target. Gram-positive-selective samples were then overlayed with 1 μl 70% formic acid. All samples were then overlaid with 1 μl of HCCA matrix. Targets were shipped to JMI laboratory and run in the Bruker BioTyper™ MALDI-TOF system. The top two matches with confidence score>1.7 were reported. All targets were processed with 24 hours of target preparation. Results are shown in Table 6.

TABLE 6

| Summary of additional co-cultures tested | | | |
|---|---|---|---|
| Species present | Initial ratio at subculture | Growth Media | Polymicrobial ID# |
| *E. coli* and *S. aureus* | 1:1, 1:10, 1:100, 1:1000, | MHB | No |
| | 10:1, 100:1, 1000:1 | MAC, MSB | Yes |
| *S. aureus* and *S. epidermidis* | 1:1, 1:10, 1:100, 10:1, 100:1 | MHB | No |
| | | MSB* +/− Abx | Yes |
| *S. lugdunensis* and *S. pneumoniae* | 1:1, 1:10, 1:100, 10:1, 100:1 | MHB | No |
| | | MSB, THB + Abx | Yes |
| *E. coli* and *P. aeruginosa* | 1:1, 1:10, 10:1 | MHB | No |
| | | MAC, CB | Yes |
| *E. coli* and *K. pneumoniae* | 1:1 | MHB | No |
| | | MAC, BpB* (Suc) | Yes |
| *S. pneumoniae* and *S. bovis* | 1:1 | MHB | No |
| | | THB, SEB | Yes |
| *S. aureus* and *M. luteus* | 1:1 | MHB | No |
| | | MSB + Abx | Yes |
| *K. pneumoniae* and *P. aeruginosa* | 1:1 | MHB | No |
| | | MAC, CB | Yes |
| *E. faecalis* and *E. faecium* | 1:1 | MHB | No |
| | | MSB, BpB* (Ara) | Yes |
| *P. aeruginosa* and *A. baumannii* | 1:1 | MHB | No |
| | | MAC, LP | Yes |

What is claimed is:

1. A method for assessing the microbial status of a patient sample as monomicrobial or polymicrobial which comprises, (a) inoculating a growth control reservoir and each of at least eight (8) reservoirs of a selective/differential growth panel (SDGP) with a cultured patient sample, said sample having been confirmed positive for microbial growth, wherein each of the 8 reservoirs comprises a distinct differential or selective growth medium for a selected microorganism or group of microorganisms, wherein the selective growth medium comprises (i) one or more compounds suitable for promoting growth of one of said selected microorganisms or group of microorganisms, (ii) one or more compounds that inhibit growth of one of said selected microorganisms or group of microorganisms, or (iii) both (1) and (ii), and wherein the differential growth medium comprises a substrate for an enzyme expressed by one of said selected microorganisms or group of microorganisms, and reaction of the substrate catalyzed by said enzyme produces a reaction product;

(b) incubating the SDGP for a time and under conditions for microbial growth to be detectable in the growth control reservoir;

(c) performing at least two different assays with each of the at least 8 reservoirs of the SDGP, wherein the assays are for independently detecting one or more of (i) the presence, absence or identity of a microorganism or a group of microorganisms in a selective or differential growth media, (ii) an amount of substrate in a differential growth media, or (iii) an amount of reaction product in a differential growth media, (d) determining from the assay results whether one of the selected microorganisms or groups of microorganisms is present in each reservoir, and (e) assessing (i) the patient sample as at least monomicrobial if all of the assays are negative, as monomicrobial or polymicrobial if at least one assay is positive, and as polymicrobial if two or more different assays are positive and (ii) the identity of the microorganisms or group of microorganisms in the patient sample, if determinable by one of said assays.

2. The method of claim 1, further comprising performing a coagulase assay and based on the results of the coagulase assay and the results from the selective and differential media, further assessing the microbial status of the patient sample as monomicrobial or polymicrobial.

3. The method of claim 1, wherein the SDGP comprises a minimum 10, 12, 14, 16, 18, or 20 reservoirs.

4. The method of claim 1, wherein one or more additional reservoirs on the SDGP comprises non-selective media.

5. The method of claim 1, wherein said SDGP is configured for detecting a Gram positive microorganism or a group of Gram positive microorganisms or a Gram negative microorganism or a group of Gram negative microorganisms.

6. The method of claim 1, wherein at least one SDGP reservoir comprises at least one probe compound.

7. The method of claim 6, wherein said probe compounds is a surface-binding agent, a locked nucleic acid, a peptide nucleic acid, or a fluorescence in situ hybridization probe.

8. The method of claim 7, wherein said probe compound comprises one or more optical labels.

9. The method of claim 1, wherein the assay for detecting the identify of a microorganism or a group of microorganisms comprises generating a mass spectrum and comparing the mass spectrum to one or more libraries of standard mass spectra for the microorganism or the group of microorganism.

10. The method of claim 9, wherein generating a mass spectrum utilizes one or more of the following: a time-of-flight (TOF) detector, a static electric and/or magnetic sector as a mass analyzer, a quadrupole mass analyzer, and an ion trap.

11. The method of claim 9, wherein generating a mass spectrum utilizes one or more of the following ionization sources: chemical ionization, plasma and glow discharge, electron impact, electrospray ionization, desorption electrospray ionization, fast-atom bombardment, field ionization, laser ionization, liquid-extraction surface analysis, and matrix-assisted laser desorption ionization.

12. The method of claim 9, wherein generating a mass spectrum comprises spotting a subsample from a reservoir of the SDGP onto a plate for matrix-assisted laser desorption ionization TOF mass spectrometry (MALDI-TOF), and performing MALDI-TOF, thereby generating the mass spectrum.

13. The method of claim 12, wherein analysis of the mass spectrum identifies proteins and/or glycolipids of the microorganism or the group of microorganisms.

14. The method of claim 12, wherein the microorganisms in a reservoir are concentrated before spotting on the MALDI-TOF target.

15. The method of claim 12, wherein one or more biochemical assays are performed before MALDI-TOF is performed.

16. The method of claim 1, wherein the patient sample is one or more of the following: blood, urine, cerebrospinal fluid, synovial fluid, an aspirate, a lavage, a wound swab, or a respiratory sample.

17. The method of claim 1, wherein two or more sets of the same SDGP reservoirs are present on a consumable such that two or more patient samples may be inoculated into that consumable.

18. The method of claim 1, wherein the assay for detecting the identify of a microorganism or a group of microorganisms comprises identifying a nucleic acid of the microorganism or the group of microorganisms.

19. The method of claim 18, wherein the assay comprises sequencing the nucleic acid, hybridizing a probe to the nucleic acid, or performing an enzyme catalyzed reaction on the nucleic acid.

20. The method of claim 1, wherein each selective medium comprises one or more media selected from the group consisting of: *Streptococcus* enrichment broth, Fraser broth, Giolitti Cantoni broth, *Streptococcus faecalis* media, sodium lauryl sulfate, tellurite, brilliant green media, brain heart infusion media with vancomycin, MacConkey media and purple media, bile esculin media, BCYE selective media with CCVC or CAV, BBE/LKV, Klinger iron media, triple sugar media, indole media, DNAse test media, Mio medium, phenol red media, eosin-methylene blue media, urea media, mannitol salt media with oxacillin, mannitol salt media without oxacillin, selective strep media, cetrimide media, and Leeds *Acinetobacter* media.

* * * * *